United States Patent [19]
Lobl et al.

[11] Patent Number: 5,192,746
[45] Date of Patent: Mar. 9, 1993

[54] CYCLIC CELL ADHESION MODULATION COMPOUNDS

[75] Inventors: Thomas J. Lobl, Encinitas; Shiu-Lan Chiang; Pina M. Cardarelli, both of San Diego, all of Calif.

[73] Assignee: Tanabe Seiyaku Co., Ltd., Osaka, Japan

[21] Appl. No.: 550,330

[22] Filed: Jul. 9, 1990

[51] Int. Cl.$^5$ .................. A61K 37/02; C07K 5/00; C07K 7/00; C07K 15/00
[52] U.S. Cl. .............................. 514/11; 514/9; 514/15; 514/16; 514/17; 530/317; 530/328; 530/329; 530/330
[58] Field of Search .............. 514/11, 13, 14, 15, 514/16, 17, 18, 9; 530/330, 329, 328, 327, 326, 325, 317

[56] References Cited

U.S. PATENT DOCUMENTS 4,792,525 12/1988 Ruoslahti et al. ............ 435/240.243

OTHER PUBLICATIONS

Lam et al., J. Bio. Chem, vol. 262, No. 3, 1987, pp. 947-950.
Pierschbacher et al., J. Biol. Chem., vol. 262, 1987, pp. 17294-17298.

*Primary Examiner*—Lester L. Lee
*Assistant Examiner*—A. M. Davenport
*Attorney, Agent, or Firm*—Spensley Horn Jubas & Lubitz

[57] ABSTRACT

Cyclized integrin receptor antagonist compounds useful in modulating cell adhesion to integrin receptors, including adhesion related to fibronectin and/or fibronectin receptors, are disclosed. Methods for synthesizing, testing, formulating, and using the compounds as therapeutic agents are also disclosed.

15 Claims, 3 Drawing Sheets

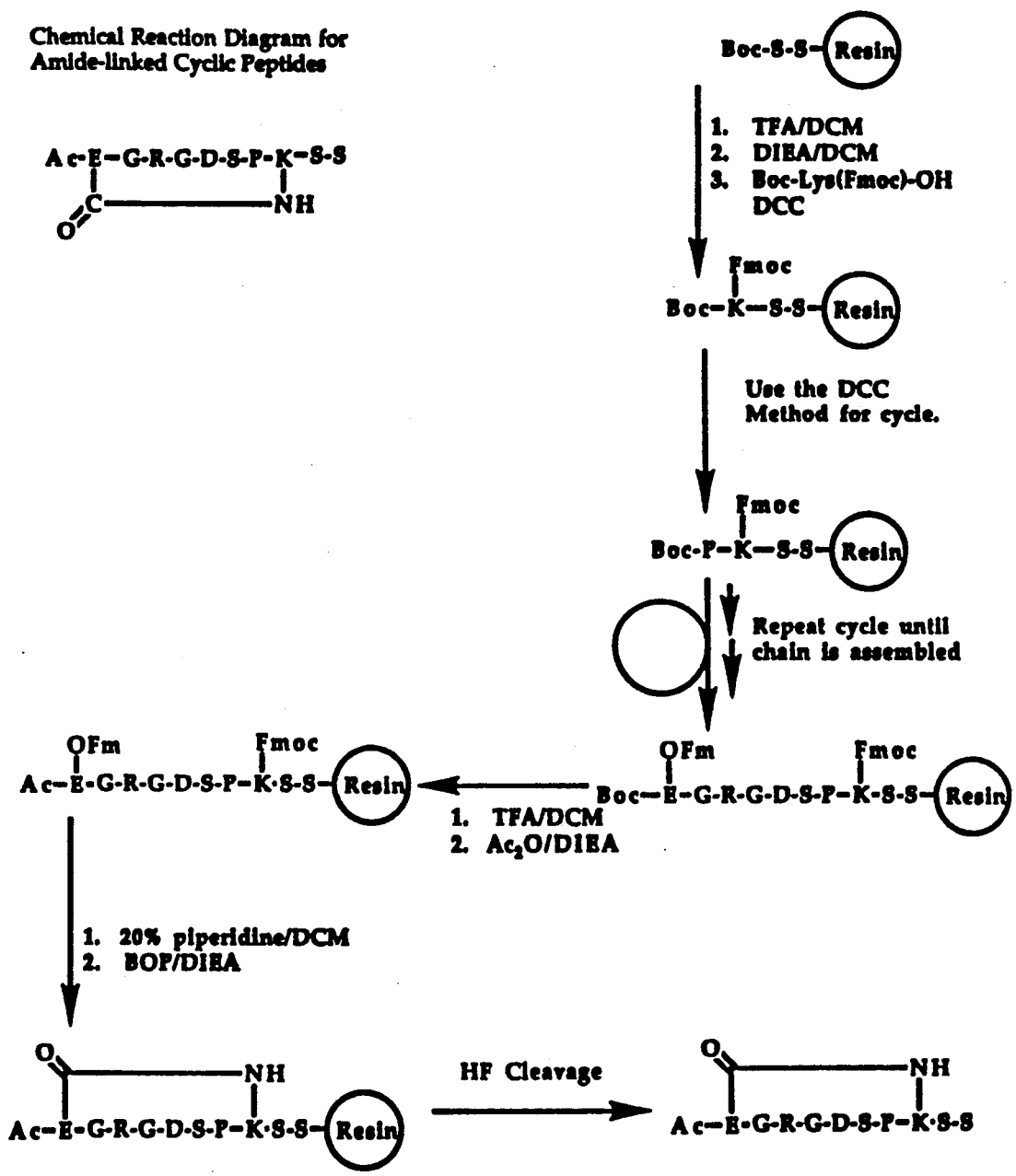

Figure 1b.

Chemical Reaction Diagram for
Amide-linked Cyclic Peptides that are
cyclized when partially assembled on-resin

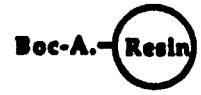

1. TFA/DCM
2. DIEA/DCM
3. Boc-Glu(OFm)-OH
   DCC

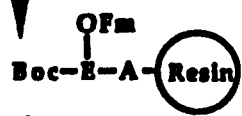

Use the DCC
Method for cycle.

1. TFA/DCM
2. DIEA/DCM
3. Boc-Pro/DCC

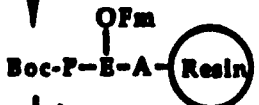

↓↓ Repeat cycle until the
   part of the chain to be
   cyclized is assembled

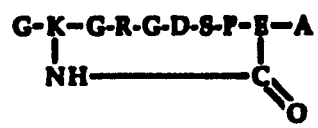

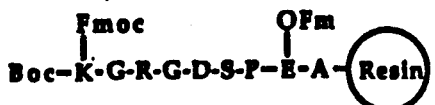

1. 20% piperidine/DCM
2. BOP/DIEA/DMF

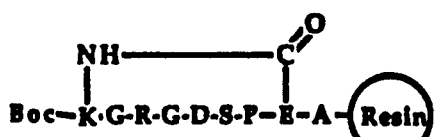

1. TFA/DCM
2. DIEA/DCM
3. Boc-Gly/DCC

↓

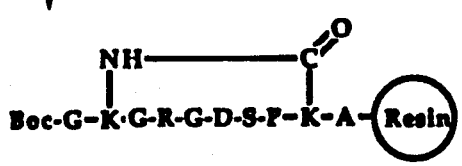

1. TFA/DCM
2. DIEA/DCM
3. HF Cleavage

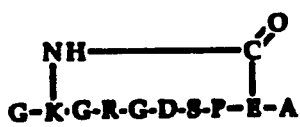

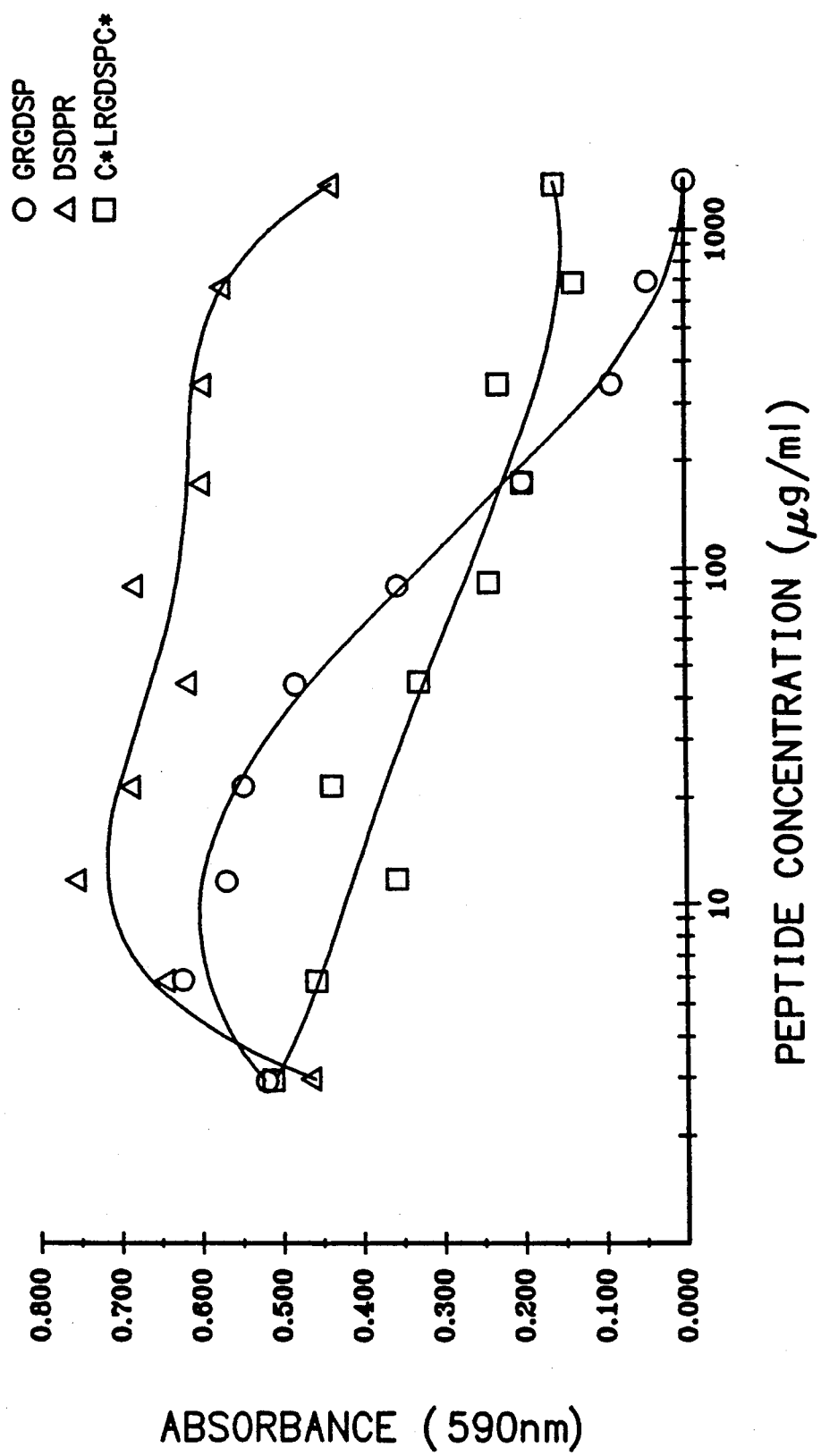

CYCLIC CELL ADHESION MODULATION COMPOUNDS

FIELD OF INVENTION

The present invention relates to novel cyclic peptides and peptidomimetic compounds which are characterized by cell adhesion modulation activity. The compounds have application to the study and treatment of disease conditions mediated by cell adhesion. Specifically, the compounds have application to the study, diagnosis, treatment or prevention of diseases and conditions such as, for example, cardiovascular disease, harmful platelet aggregation, neoplastic disease including metastasis of neoplastic growth, wound healing, inflammation and autoimmune disease or other diseases or conditions involving cell adhesion.

BACKGROUND OF THE INVENTION

The extracellular matrix is that material which surrounds the muscle and is the major component of connective tissue of all mammals. The extracellular matrix provides for structural integrity, and promotes cell migration and cellular differentiation. As part of these functions, the extracellular matrix has been shown to support adhesion for various types of cells in vitro. Molecules such as the collagens, fibronectin, vitronectin, laminin, von Willebrand factor, thrombospondin, bone sialoprotein, fibrinogen, and tenacin have been found to possess this property of mediating cell adhesion.

The above cell-adhesive molecules have been found to exhibit a structural similarity in their respective binding sites, each of which contains the amino acid sequence arginine-glycine-aspartic acid, or RGD using single letter nomenclature (infra). The cell-binding site in fibronectin has been reproduced synthetically. In turn, the cellular receptor site for fibronectin has been identified for various cells. In addition, cellular receptors that recognize RGD-containing sequences in other extracellular matrix proteins (e.g., the vitronectin receptor) have been identified.

Such cellular receptors, responsive to RGD-containing proteinaceous compounds, have been characterized. The complete, primary structure of the fibronectin receptor has been deduced from cDNA, and physical properties have been determined. Argraves, et J.Biol. Chem. 261: 12922 (1986); Argraves J.Cell Biol. 105: 1183 (1987). The protein exists at the cell surface as a heterodimeric complex (although the larger polypeptide is enzymatically processed) having both polypeptide chains inserted into the membrane. Each chain extends 30-40 residues into the cytoplasmic space, and at least one of the cytoplasmic peptides appears to interact with the cytoskeleton. Horwitz et al., Nature 320: 531 (1986). The larger of the two polypeptides, the $\alpha$ subunit, contains a number of regions that are structurally similar to calmodulin and that apparently mediate the binding of calcium to the receptor. The presence of such divalent cations is required for the receptor to bind ligand. The $\beta$ subunit is somewhat smaller and conformationally compact due to numerous intrachain disulfide bonds. The cytoplasmic domain of the $\beta$ subunit contains a potentially phosphorylated tyrosine. Hirst et al., PNAS-USA 83: 6470 (1986); Tamkun et al., Cell 46: 271–282 (1986).

Other RGD-directed receptors, as well as other "orphan" receptors the ligand for which is unknown, have also been characterized. This putative RGD commonality of the ligand matrix proteins has revealed a superfamily of cell surface receptor proteins that share a high degree of structural similarity and probably also functional similarity. The members of this superfamily of cell surface proteins collectively are known as the integrins. The integrins can be grouped on the basis of the identity of their $\beta$ subunit. The $\beta$ subunit, as disclosed above for the fibronectin receptor, is compact due to a high degree of cross-linking. The first group of integrins includes the very late activation antigen (VLA) proteins, which themselves include the fibronectin receptor (VLA-5), the collagen receptor (VLA-2), and the laminin receptor. The second group includes the lymphocyte associated antigen-1 (LFA-1), macrophage antigen-1 (MAC-1), and p150,95. The third group includes the vitronectin receptor, and platelet glycoprotein gpIIb/IIIa. Hynes, Cell 48: 549 (1987); Hemler, Immunol. Today 9: 109 (1988); Springer et al., Annu. Rev. Immunol. 223 (1987); Kishimoto et al., Leukocyte Integrins, in: Leukocyte Adhesion Molecules, T. A. Springer, D. C. Anderson, A. S. Rosenthal, and R. Rothlein, Eds., Springer-Verlag, New York, pp. 7–43 (1989).

The RGD-directed receptor present on platelets that binds fibronectin, vitronectin, fibrinogen, and von Willebrand factor has also been purified. This receptor is the gpIIb/IIIa protein complex. This receptor is thus not specific to one extracellular matrix protein, as are the above fibronectin and vitronectin receptors. It has been proposed that this lack of specificity is correlated to the lack of conformational specificity in the ligands. Other work has suggested that specificity can be achieved with relatively short, conformationally restricted synthetic peptides containing the RGD sequence. For a literature summary, see: Pierschbacher et al., Nature 309: 30 (1984); Pierschbacher et al., pNAS-USA 81: 5985 (1984); Ruoslahti et al., Cell 44: 517 (1986); Pierschbacher et al., Science 238: 491 (1987); Pierschbacher et al., J.Biol.Chem. 262: 17294 (1987); Hynes, Cell 48: 549 (1987); Ruoslahti, Ann. Rev. Biochem. 57: 375 (1988). It has also been proposed that the receptor affinity for its peptide ligand may be altered as the stereoconformation, or three-dimensional shape, of the peptide is restricted, typically by cyclization. Pierschbacher and Ruoslahti, PCT International Publication WO 89/05150 (1989). However, the publication states that the cyclic peptide of the invention (see FIG. 2 and Example V) was ineffective in inhibiting attachment to fibronectin.

A limited number of compounds containing sequences of natural amino acids or derivatives other than RGD may also possess the capability for affecting cell adhesion. These non-RGD-containing peptides are not well characterized. See. Graf, J. et al., Cell 48:989 (1987); Kloezewiak, M. et al,, Biochemistry 23:1767–1774 (1984); Wayner, E.A., et al., J. Cell. Biol. 109:1321 (1989).

All publications, patents and other reference materials to which reference is made in the present specification are incorporated herein by reference.

SUMMARY OF THE INVENTION

The present invention relates to compounds having activity as cell adhesion modulators. Some of the compounds contain the amino acid sequence arginine-glycine-aspartic acid (Arg-Gly-Asp or RGD). Others contain non-RGD sequences, including but not limited to the RCD sequence and "reverse orientation" forms of amino acid residues. The compounds, in one aspect, sufficiently mimic extra-cellular matrix ligands or other cell adhesion ligands so as to bind to cell surface receptors. Such receptors include integrin receptors in general, including the fibronectin, collagen, laminin, LFA-1, MAC-1, p150,95, vitronectin and gpIIb/IIIa receptors. The novel compounds have been found to modulate cell adhesion by competing, for example, with RGD-containing ligands and by binding to RGD-directed receptors on cell surfaces. The cell adhesive protein, such as (but not limited to) fibronectin, is sufficiently inhibited from binding to the cell's receptor as to prevent or reduce cell adhesion. Other uses include enhancing cell adhesion by using the compounds to attach cells to a surface, or by other promotion of cell adhesion. The useful compounds herein described function as cell-adhesion modulators.

One object of the present invention is to provide novel compounds which act to modulate cell adhesion.

Another object of the present invention is to provide novel RGD-containing compounds which are capable of binding with a cellular receptor.

Another object of the present invention is to provide novel non-RGD-containing compounds which are capable of binding with a cellular receptor.

Another object of the present invention is to provide novel non-RGD-containing compounds which contain one or more "reverse orientation" amino acid residues and which are capable of binding to a cellular receptor.

Another object of the present invention is to provide novel non-glycine containing, e.g., RCD-containing, compounds which are capable of binding to a cellular receptor.

Another object of the present invention is to provide new uses for known peptides containing the sequence RGD as cell adhesion modulators.

Another object of the present invention is to provide a novel method for modulating cell adhesion using novel compounds.

Another aspect of the invention is to provide compounds having extraordinarily high potencies in modulating cell adhesion to integrin receptors, including specifically inhibition of cell adhesion to the fibronectin receptor. Thus, in one regard, the present invention includes compounds having an IC$_{50}$ of less than about 500 μM as established in a U937 fibronectin adhesion assay; and in another regard, the invention includes compounds having an IC$_{50}$ of less than about 100 μM in such assay. The invention also includes methods for obtaining (either in vitro or in vivo) such fibronectin receptor adhesion inhibition, and integrin receptor adhesion inhibition generally, using disclosed compounds, at desirably low concentrations, having an IC$_{50}$ of less than about 500 μM, or alternately less than about 100 μM. Likewise, another aspect of the invention is to provide such compounds, and such methods for obtaining integrin receptors adhesion inhibition, with IC$_{50}$ potency levels at least as low as about 1 μM, and alternately at least as low as about 6.8 μM.

Another object of the present invention is to provide novel compounds, formulations, and methods which may be used in the study, diagnosis, treatment or prevention of diseases and conditions which relate to cell adhesion, including but not limited to rheumatoid arthritis, asthma, allergies, adult respiratory distress syndrome (ARDS), cardiovascular disease, thrombosis or harmful platelet aggregation, neoplastic disease including metastasis of neoplastic growth, wound healing, Type I diabetes, inflammatory conditions including ophthalmic inflammatory conditions and inflammatory bowel disease (e.g, ulcerative colitis and regional enteritis), and autoimmune diseases.

Another object is to provide derivative compounds, such as, but not limited to, antibodies and anti-idiotype antibodies to the compounds disclosed and claimed in order to study, diagnose, treat or prevent diseases and conditions which relate to cell adhesion, including but not limited to rheumatoid arthritis, asthma, allergies, adult respiratory distress syndrome (ARDS), cardiovascular disease, thrombosis or harmful platelet aggregation, neoplastic disease including metastasis of neoplastic growth, wound healing, Type I diabetes, inflammatory conditions and autoimmune diseases.

BRIEF DESCRIPTION OF THE DRAWINGS

FIGS. 1a and 1b are diagrams representing chemical reactions for the manufacture of amide-linked cyclic peptides.

FIG. 2 shows the results of an assay demonstrating cell adhesion inhibition by the representative cyclic polypeptide,

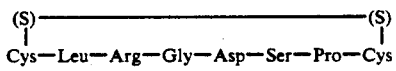

DETAILED DESCRIPTION

The compounds of the present invention are those having the property of modulating cell adhesion.

While cell adhesion is required for certain normal physiological functions, there are situations in which cell adhesion is undesirable, or in which modulated cell adhesion is desirable.

Altered leukocyte-endothelial interactions are implicated in adult respiratory distress syndrome (ARDS). Here, the attachment of inappropriate cells to the lung lining induces an inflammatory response. This results in lung injury, ARDS and in some cases, asthma. Preliminary in vitro results show that such detrimental attachment, in which the leukocyte adheres to endothelial cells or the lung extracellular matrix, is mediated by RGD-containing protein and integrin receptors on the leukocytes. In this situation, peptides or other compounds with a binding affinity to RGD receptors are desirable as competitive antagonists and should be useful in treating ARDS and asthma.

Cell adhesion also contributes to metastasis of cancerous tumors. Metastasis has been called "the major underlying cause of death from cancer." Welch, et al., Intern. J. Cancer 43: 449 (1989). An RGD-containing peptide which would prevent cell adhesion to basement membrane components may be useful to prevent or eliminate metastasis. See, Humphries, M.J. et al., Science 233:467 (1986); Liotta, L.A., Cancer Res. 46:1 (1986); Roose, E., Biochem. Biophys. Acta., 738:263 (1986). A peptide or other compound with suitable affinity for RGD receptors should likewise have anti-metastasis utility.

Harmful blood clotting is also caused by inappropriate cell adhesion, particularly cell adhesion to the extracellular matrix. The attachment, spreading and aggregation of platelets on extracellular matrices are central events in thrombus formation. These events can be regulated by the family of platelet adhesive glycoproteins, fibrinogen, fibronectin, and von Willebrand factor. Fibrinogen functions as a cofactor for platelet aggregation, while fibronectin supports platelet attachment and spreading reactions. Von Willebrand factor is important in platelet attachment to and spreading on subendothelial matrices. Plow et al., PNAS-USA 82: 8057 (1985). A peptide or other compound which would function as an antagonist and bind to cell receptors which recognize the matrix glycoprotein RGD site would be beneficial as a thrombolytic.

Other physiological conditions may be treated by stimulatory modulation of cell adhesion. Wound healing, for example, is undesirably prolonged when insufficient cell adhesion occurs. A peptide or other compound with suitable affinity for RGD receptors, attached for example to a suitably positioned matrix or surface, may be able to promote beneficial cell adhesion and resultant wound healing by binding cells with the appropriate RGD-recognizing receptor. Also, in prosthetic implantation, such peptides or other compounds coating the prosthesis would provide a means for covering the prosthesis with a surface of cells. This cell surface would provide a surface compatible with the organism, and thus minimize rejection that might otherwise occur due to stimulation of the immune system by the prosthesis itself.

The cell adhesion modulation compounds of the present invention are represented in part herein by amino acid sequence formulas wherein the individual amino acids are represented by their standard three-letter or alternately one-letter abbreviations as follows:

| Amino Acid | Three-letter symbol | One-letter symbol |
| --- | --- | --- |
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Where abbreviations such as the foregoing are used herein without an indication of enantiomeric structure, either the L- or D-enantiomers may suitably be utilized, although the L-enantiomer is preferred for amino acids having the normal (non-reversed) peptide bond orientation, and the D-enantiomer is preferred for amino acids having a reversed orientation (see discussion below).

Additional abbreviations used herein for analogs of amino acids and amino acid mimetic compounds include:

| | |
| --- | --- |
| β-Adamantylalanine | (Ada)-Ala |
| β-Alanine (3-aminopropionic acid) | β-Ala |
| α-Aminoisobutyric acid (2-methylalanine) | Aib |
| D-3-(2'-Naphthyl)alanine | D—Nal |
| 3,4-Dehydroproline | Dhp |
| Gamma-aminopentane-1,5-dioic acid | 3-Glu |
| Homoarginine | homoArg |
| Homoproline | homoPro |
| Homoserine | homoSer |
| 4-Hydroxyproline | Hyp |
| 3-Mercaptopropionic acid (des-α-amino cysteine) | Mpr |
| 1-β-Mercapto-β,β-cyclopentamethylenepropionic acid | PMP |
| Nicotinyl lysine | Nic—Lys |
| Norarginine ($H_2NC(=NH)NH(CH_2)_2CH(NH_2)CO_2H$) | norArg |
| Norleucine | Nle |
| Ornithine | Orn |
| Penicillamine (β,β-dimethylcysteine) | Pen |
| Pyroglutamic acid | pyroGlu |
| Sarcosine | Sar |
| 3-Thioproline | 3-thioPro |

Additional abbreviations used herein include:
1,1-ACC, 1-Amino-1-cyclohexanecarboxylic acid
Ada, adamantane
(Ada)-Ac, 1-Adamantaneacetic acid
(Ada)-CA, 1-Adamantanecarboxylic acid
ARDS, Adult respiratory distress syndrome
BOC, tert-butyloxycarbonyl
BSA, Bovine serum albumin
Cbz, Benzyloxycarbonyl
Chx, Cyclohexyl ester
DCC, dicyclohexylcarbodiimide
DCM, Dichloromethane
DMF, Dimethylformamide
DIEA, Diisopropylethylamine
Fm, Fluorenylmethyl ester
FMOC, Fluorenylmethyloxycarbonyl
FN, Fibronectin
ICAM-1, Intercellular adhesion molecule 1
$IC_{50}$, Inhibitory concentration, concentration at which adhesion is inhibited to 50% of control level
IPA, isopropyl alcohol
(NB)-Ac, 2-Norbornaneacetic acid
(norAda)-CA, 3-Noradamantanecarboxylic acid
TEA, Triethylamine
TFA, Trifluoroacetic acid
VLA, Very late activation antigens A. Cyclic Normal Orientation Compounds The first class of compounds of the invention is represented by the formula:

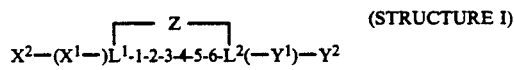

(STRUCTURE I)

and pharmaceutically acceptable salts thereof, wherein
$L^1$ and $L^2$ are each, or are together, a residue of an amino acid, an amino acid analog or an amino acid mimetic having a functional group suitable for the formation of a cyclizing bridge between $L^1$ and $L^2$;

Z is a cyclizing moiety or bond between $L^1$ and $L^2$;

1 is optional and, where present, is selected from Leu, Tyr, Phe, Ile, Pro, Gly, Ala, Val, norLeu, norVal, β-Ala, Trp, D-Nal, Sar and (Ada)-Ala;

2 is selected from Arg, N-methylArg, homoArg, and norArg;

3 is selected from Gly, and Sar;

4 is selected from Asp and, where 2 is norArg, Glu;

5 is optional and, where present, is selected from Ser, Thr, Tyr, Trp, Ala, Val, Phe,

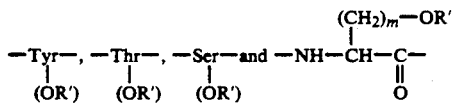

wherein m is 2, 3 or 4;

6 is optional and, where present, is selected from Pro, 3-thioPro, 1,1-ACC, Dhp, Hyp, homoPro and Phe;

$X^1$ and $Y^1$ are each optional and, where present, are independently selected from sequences of from 1 to 4 D- or L-amino acids and amino acid analogs;

$X^2$ is an optional $N^\alpha$-substituent selected from R' (including hydrogen) and R'CO—;

$Y^2$ is an optional carboxyl-terminal substituent selected from —OR' (including hydroxyl), —NR'$_2$ (including —NH$_2$ and —NHR'), —NHNH$_2$ and —SR';

and wherein each R' is individually a pharmaceutically suitable substituent group, preferably one selected from hydrogen, from linear and branched, unsubstituted and substituted $C_1$-$C_8$ lower alkyls, $C_2$-$C_8$ alkenyls, $C_2$-$C_8$ alkynyls, $C_6$-$C_{14}$ aryls, $C_7$-$C_{14}$ alkaryls, $C_7$-$C_{14}$ alkaryls and $C_3$-$C_{14}$ cycloalkyls, and, in the case of —NR'$_2$, from cyclized groups forming (in an attachment with the nitrogen atom) a 5–8 membered heterocyclic ring optionally containing oxygen, nitrogen or sulfur as a further ring heteroatom.

In the above structure I, a bridge is formed via the cyclizing moiety Z between $L^1$ and $L^2$ such that the compound is cyclized. (It will be appreciated, both here and in structures depicted below in this disclosure, that the angular corners on connecting lines such as those shown in Structure I as linking Z with $L^1$ and $L^2$ are not intended, at the corners, to represent methylene residues.) Therefore, each of $L^1$ and $L^2$ is chosen so as to provide a functional group suitable for the formation of a cyclizing bridge. As is discussed in more detail hereinafter, preferred functional groups include thiol, amino and carboxyl groups and their residues. Such a functional group may be provided by the side-chain, or by the terminal α-amino (in $L^1$) or terminal carboxyl (in $L^2$) group, of a natural amino acid residue or an analog thereof (including a homolog or stereoisomer thereof; see e.g. Table 1 above); or it may be provided by an "amino acid mimetic" moiety, i.e., an organic residue which includes a suitable cyclizing functional group and which is covalently linked through a peptide (i.e., amide) bond to the amino terminus (in the case of $L^1$) and/or to the carboxyl terminus (in the case of $L^2$) of the residue sequence (NH$_2$—)1-2-3-4-5-6(—COOH).

The bridging residues $L^1$ and $L^2$ are, in one embodiment, each preferably selected from Cys, Pen, homoCys, and, for $L^1$, des-α-aminoCys and PMP. Each of these residues provides a side chain sulfhydryl group particularly suitable as a reactive precursor functional group for the formation of a cyclizing bridge between $L^1$ and $L^2$. Specifically, in the case of these residues, the cyclic bridge may be formed via oxidative coupling (loss of hydrogens) to form a disulfide bond between the side chain sulfur groups (in which the cyclizing moiety Z is a simple bond between the two sulfur atoms). This may also be depicted generally for compounds wherein, for example, both $L^1$ and $L^2$ are Cys residues as follows:

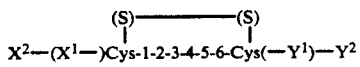

wherein (as in other similar depictions used herein) the side chain functional group portion (here, a sulfur atom in both instances) appears in parentheses above the residue having the side chain.

It is particularly preferred in such embodiments that $L^1$ and $L^2$ be Cys or Mpr. The combination of $L^1$=Pen and $L^2$=Cys is, in embodiments containing the sequence Arg-Gly-Asp, not preferred in the practice of the present invention.

The cyclizing bridge may also be formed via a hydrocarbon moiety, for example a (poly)methylene bridge moiety of the form —(CH$_2$)$_n$— where n is an integer of from 1 to 8, preferably 1 to about 4. One type of such bridge is represented below, wherein a cyclic compound with three methylene residues (representing Z) between two cysteine side-chain sulfur atoms (representing $L^1$ and $L^2$) is depicted:

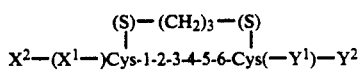

See L. Fieser and M. Fieser, Reagents for Organic Synthesis Vol. 1, pages 356–357 (J. Wiley and Sons, Inc. 1967); Fieser, J. Amer. Chem. Soc., 76:1945 (1954).

In other preferred embodiments of the invention, diketo and diamino linking groups Z such as those of the form

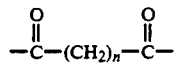

and

wherein n is as defined above, may also conveniently be used to link, for example, side chain amino (as in Lys) or carbonyl (as in Glu or Asp) residues, respectively, on $L^1$ and $L^2$ to yield structures exemplified by

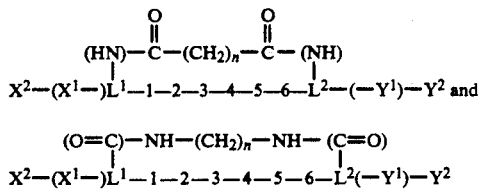

(Here, as elsewhere, the side chain functional groups (amino and carbonyl) on $L^1$ and $L^2$ are depicted in parentheses above the residue abbreviation.)

The foregoing are but examples of suitable hydrocarbon-containing bridges, and other forms will also be apparent to those skilled in the art. Where the cyclizing moiety Z includes a portion with such a hydrocarbon form, it may be branched and may, where of a size appropriate to form a stable structure (particularly, where Z comprises two or more methylene moieties) also include one or more heteroatom-containing substituents including hydroxyl, amino, nitro, alkoxyl and halo substituents. Such substituents may be used to affect the solubility and/or biodistribution characteristics of the subject compounds. Aromatic or cycloalkyl hydrocarbon-containing bridge groups may also be utilized in the Z position, as for example diketo or diamino structures such as

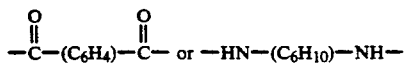

Simple hydrocarbon moieties of from 1 to about 4 carbons are preferred for hydrocarbon portions of such Z-moieties.

The cyclizing bridge between $L^1$ and $L^2$ may also be formed via a monosulfide (thioether) linkage, as exemplified below.

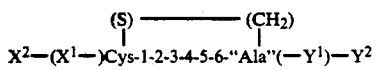

In such a case, $L^1$ can be formed from a residue of $\alpha,\beta$-dehydroalanine, and $L^2$ from a residue of cysteine, which may be reacted to yield a lanthanide-like thioether linkage. In this regard, see Palmer, et al., "Conformational Studies," in *Peptides—Chemistry, Structure Biology*, Rivier & Marshall, eds., Escom. Leider, pp. 616–618 (1990), and Jung, "Peptides With Sulfide Bridges and Dehydroamino Acids," op. cit., pp. 865–869.

Alternatively, $L^1$ and $L^2$ may be chosen from other amino acids or analogs or amino acid mimetics which provide functional groups suitable for the formation of a cyclizing bridge. Such functional groups may occur on the side chain or as the amino- or carboxyl-terminus of an amino acid or analog residue. For example, $L^2$ may be selected from Asp, Glu, or other amino acids or analogs which provide a suitable side chain carboxyl group for cyclic linkage, through formation of an amide bond in a condensation reaction, with an amino group (e.g., an $N^\alpha$-amino group, or a side chain amino group as on, for example, Lys or Orn) on $L^1$, provided, however, that the structure

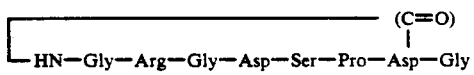

is not included. The cyclizing moiety Z will in such cases be a simple bond between $L^1$ and $L^2$. Likewise, an amino acid residue $L^2$ may provide a carboxyl group from its carboxyl terminus for amide linkage with either a side chain amino or $\alpha$-amino group on an amino acid residue or analog $L^1$; or the direction of the amide linkage may be reversed where $L^1$ provides a side chain carboxyl group and $L^2$ provides a side chain amino group. Such structures may be exemplified as follows:

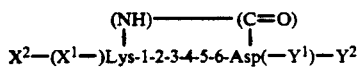

[wherein the side chain amino and carbonyl groups of $L^1$ (Lys) and $L^2$ (Asp) are directly bonded];

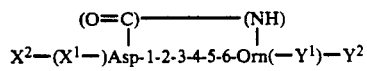

[wherein amide bond direction (from side chains of $L^1$ and $L^2$) is reversed];

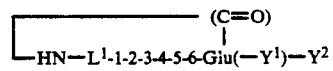

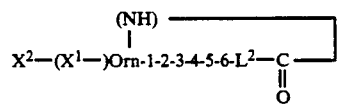

[wherein the depicted amino terminus of $L^1$ is directly bonded to the side chain carboxyl group of Glu ($L^2$), or the depicted carboxyl terminus of $L^2$ is directly bonded to the side chain amino group of Orn ($L^1$); here, as elsewhere, the corners of the bent connecting line depicting these bonds do not represent methylene groups];

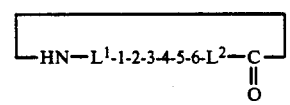

[wherein the depicted $\alpha$-amino terminus at $L^1$ is directly bonded to the depicted carboxyl terminus at $L^2$, such that an amide bond is formed in the peptide "backbone" of the compound].

Analogs of amino acid residues may also be utilized for $L^1$ and/or $L^2$, as for example homologs (wherein a side chain is lengthened or shortened while still providing a carboxyl, amino or other reactive precursor functional group for cyclization), D-enantiomers of amino acids, analogs having variant side chains with appropriate functional groups (as for example $\beta$-cyanoalanine, canavanine, djenkolic acid, L-azaserine or gammamethyleneglutamic acid), or other amino acid analogs (see for example the table of amino acid analogs and mimetic compounds given above).

Amino acid mimetic structures that are capable of being covalently bonded through an amide bond to a carboxyl and/or amino terminus of the residue sequence 1-2-3-4-5-6, and which provide a suitable precursor functional group for cyclization (through Z), may also be employed in positions $L^1$ and/or $L^2$. Such amino acid mimetic structures include organic species containing one or more heteroatoms including at least one functional group (preferably a reactive heteroatom-containing functional group) precursor suitable for cyclization. Examples include residues of the form

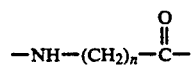

wherein n ranges from 1 to about 8, and preferably from 1 to 4, as for example residues of $\beta$-alanine and gamma-aminobutyric acid. (Where n is 1, the amino acid glycine, rather than an $\alpha$-amino acid mimetic, results.) Such a structure may, similar to the amino acids and amino acid analogs discussed above, be utilized as $L^1$ (wherein the carbonyl group depicted above, formed for example from a carboxyl precursor, conveniently forms an amide (peptide-mimetic) linkage with the amino terminus of residue 2 or, if present, residue 1), or it may be utilized as $L^2$ (wherein the depicted amino group may engage in an amide linkage with the carboxyl terminus of the terminal residue 4, 5 or 6). If only one such linking residue L is used, it may serve as both $L^1$ and $L^2$ (and thereby include Z) in that cyclization can be achieved through formation of two amide bonds, one at each terminus of the sequence 1-2-3-4-5-6. Such structures may be exemplified by the form

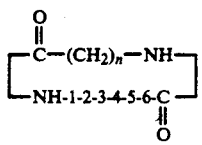

where the $N^\alpha$-terminus and the carboxyl terminus of the sequence 1-2-3-4-5-6 are bonded directly to, respectively, the carbonyl residue and the amino residue of the amino acid mimetic linking group depicted immediately above to form two peptide-mimetic amide bonds. Likewise, cyclization can be achieved with such an amino acid mimetic linking moiety wherein a side chain functional group on a second linking moiety appended (as $L^1$ or $L^2$) to one terminus of the numbered sequence 1-2-3-4-5-6 (as for example an amino or carboxyl side chain group) engages in bonding to the mimetic moiety, and the mimetic moiety (as $L^2$ or $L^1$) cyclizes the compound to the remaining terminal residue of the numbered sequence. This may be exemplified by structures of the form

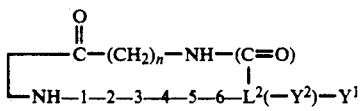

wherein $L^2$ (as for example Asp) provides the side chain carbonyl group depicted in parenthesis, residue 1 provides the depicted $N^\alpha$-terminal amino group, and the amino acid mimetic linking moiety

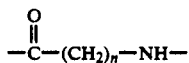

serves as $L^1$.

Amino acid mimetic structures containing aromatic, cycloalkyl or other linking portions can also be utilized as $L^1$ and/or $L^2$, such as structures of the form

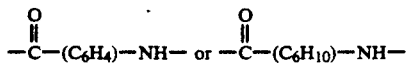

Similarly, the heterobifunctional (keto-amino) structures depicted above may also serve as a Z-group in linking complementary side chain functional groups on $L^1$ and $L^2$ (e.g., a side chain amino group on $L^1$ and a side chain carboxyl group on $L^2$) through two amide bond structures.

As will be discussed in more detail below, homobifunctional structures such as those of the form

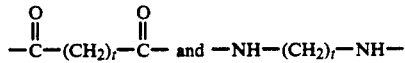

where t is an integer of from 1 to about 8, and more preferably 1 to 3, may also serve individually as amino acid mimetic structures where a "reverse" amino acid sequence occurs within the structure 1-2-3-4-5-6 (see Structures II and III below). In such cases, the numbered portion of such a structure will display two carboxyl termini or two amino termini (rather than one of each type), and $L^1$ and $L^2$ may be selected together to be a homobifunctional linking moiety such as one of those depicted above.

Other forms of cyclization include those wherein Z comprises a secondary amino structure (obtained, for example, upon reduction of the carbonyl portion of an amide linkage to a methylene group). For example, a secondary amino linking structure may be formed by reaction of an aldehyde functional group on $L^1$ (e.g., an aldehyde formed by reduction of a side chain carboxyl group on Asp or Glu) or on $L^2$ (e.g., an aldehyde formed from the terminal carboxyl group of $L^2$) with a suitable amino group (on, e.g., the side chain or $N^\alpha$-terminus of $L^2$ or $L^1$). Methods for the preparation and incorporation of such aldehyde-bearing residues in peptide structures are described by Fehrentz, J-A and Castro, B., in Synthesis 676–678 (1983), and by Sasaki, Y. and Coy, D.H., in Peptides 8:119–121 (1987). Thus, where the carboxyl terminus of $L^2$ is of the reduced aldehyde form and is bonded to the amino terminus of $L^1$ in a reductive alkylation reaction, a peptide bond isostere structure ($-NHCH_2-$) will result in the cyclic backbone of the product.

Other means of cyclization through appropriate choices of $L^1$, $L^2$ and Z will be recognized by those skilled in the art and are included in the scope of the present invention.

It is also specifically contemplated that the foregoing discussion of cyclizing moieties (Z), bridging residues ($L^1$ and $L^2$), substituents, amino acid analogs, amino acid mimetics, cyclization methods, and the like are applicable, mutatis mutandis, to the other structural formulas discussed hereinafter.

Residue 1 in structure I is most preferably Leu; residue 2 is most preferably Arg; residue 3 is most preferably Gly; residue 4 is most preferably Asp; residue 5 is most preferably Ser; and residue 6 is most preferably Pro. The sequence Leu-Arg-Gly-Asp-Ser-Pro is most preferred for residues 1-2-3-4-5-6.

Also preferred for residue 4 is Glu where residue 2 is norArg. Thus, the sequence Leu-norArg-Gly-Glu-Ser-Pro is also preferred for residues 1-2-3-4-5-6.

$X^1$ and $Y^1$ are each optional in structure I. Where present, they are preferably each independently selected so as to enhance the activity of the resultant compound and/or to preserve the compound against metabolism in, for example, the D vivo environment and thereby increase the effective half-life of the compound. In this regard, the use of one or more D-amino acids, most preferably at one or more terminal residue position in the compound (i.e., at the amino-most and-/or carboxyl-most residue position in $X^1$ or $Y^1$) are believed to stabilize the compound against metabolism by proteolytic or other enzymes in the body. Specific preferred residues for position $X^1$ include Gly-, Phe-, Leu-, Asn-, Val-, Tyr, 1- or 2-naphthylalanine, cyclohexylAla-, 3-aminobutyric acid, Aib-, Ser-Tyr-Asn-, Ala-Thr-Val-, and p-Cl-Phe-. Preferred residues for position $Y^1$ include -Ala, -Ala-Ser, -Ala-Ser-Ser, -Ala-Ser-Ser-Lys, -Ala-Ser-Ser-Lys-Pro, -Thr, -Thr-Phe, -Aib, -p-Cl-Phe, -(3-aminobutyric acid), or 2-naphthylalanine, and -(cyclohexylAla). Such $X^1$ and $Y^1$ groups are preferred also in the corresponding positions given in the structural formulas described hereinafter.

Where a substituent $X^2$ or $Y^2$ incorporating $R'$ other than hydrogen is used, e.g., acyl groups $R'CO$ or amino groups of the form $R'NH$, preferred substituents include those derived from bulky groups such as adamantaneacetic acid, 2-naphthylacetic acid, 2-norbornaneacetic acid, 3-noradamantanecarboxylic acid, and 1- or 2-adamantylamine.

Structures exemplified by the forms $$-Tyr-, -Thr- \text{ and } -Ser-$$
$$\phantom{-Tyr-,}\; (OR')\quad (OR')\quad\; (OR')$$

such as those set forth with respect to residue 5 in Structure I, represent derivatives of amino acid residues

```
      (S)―――――――――――――――(S)
       |                    |
Gly―Cys―Leu―Arg―Gly―Asp―Ser―Pro―Cys―NH2
```

```
         (S)―――――――――――――(S)
          |                  |
(Ada)―Ac―Gly―Cys―Arg―Gly―Asp―Ser―Pro―Cys
```

```
   (S)――――――――――――――(S)
    |                   |
Cys―Sar―Arg―Gly―Asp―Ser―Pro―Cys
```

```
   (S)――――――――――――(S)
    |                |
Mpr―Arg―Gly―Asp―Ser―Pro―Cys
``` wherein the side chain hydroxyl group (shown in parentheses) is optionally substituted with a group of the form $R'$ which can be other than hydrogen as defined above.

Where such substituted residues are employed in position 5 of structure I, $R'$ is preferably selected from hydrogen and $C_1$ through $C_8$ lower alkyls, particularly methyl and ethyl alkyl moieties.

A particularly preferred compound within the scope of structure I includes:

```
  (S)―――――――――――――――(S)
   |                    |
Cys―Leu―Arg―Gly―Asp―Ser―Pro―Cys
``` wherein the shorthand structure $$\begin{array}{c}(S)\\|\\-Cys-,\end{array}$$

consistent with similar usage elsewhere in this description, represents a cysteine residue with its side chain sulfur atom separately depicted, and likewise the structure (S)—(S) represents a disulfide bond. The compound depicted has been shown to be active in inhibiting cell adhesion to fibronectin.

Other preferred compounds within the scope of structure 1 include:

```
         (S)―――――――――――――――(S)
          |                    |
Ac―Gly―Cys―Leu―Arg―Gly―Asp―Ser―Pro―Cys―NH2
```

```
      (S)――――――――――――――(S)
       |                   |
D―Nal―Cys―Arg―Gly―Asp―Ser―Pro―Cys―NH2
```

```
   (S)――――――――――――(S)
    |                |
Cys―Arg―Gly―Asp―Tyr―Pro―Cys
```

```
   (S)――――――――――――――(S)
    |                  |
Mpr―Tyr―Arg―Gly―Asp―Ser―Pro―Cys
```

```
              (S)―――――――――――(S)
               |               |
(Ada)―Ac―Gly―Gly―Cys―Arg―Gly―Asp―Ser―Pro―Cys
```

```
              (S)―――――――――――――――(S)
               |                    |
(Ada)―Ac―Gly―Gly―Cys―Arg―Gly―Asp―Tyr-3-thioPro―Cys―NH2
```

```
              (S)―――――――――――――――(S)
               |                    |
(Ada)―CA―Gly―Gly―Cys―Arg―Gly―Asp―Tyr-3-thioPro―Cys―NH2
```

```
              (S)―――――――――――――(S)
               |                  |
(Ada)―CA―Gly―Gly―Cys―Arg―Gly―Asp―Tyr―Pro―Cys―NH2
```

```
              (S)―――――――――――――(S)
               |                  |
(Ada)―Ac―Gly―Gly―Cys―Arg―Gly―Asp―Tyr―Pro―Cys―NH2
```

```
                 (S)―――――――――――――――(S)
                  |                    |
(norAda)―CA―Gly―Gly―Cys―Arg―Gly―Asp―Tyr-3-thioPro―Cys―NH2
```

```
             (S)―――――――――――――(S)
              |                  |
(NB)―Ac―Gly―Gly―Cys―Arg―Gly―Asp―Tyr―Pro―Cys―NH2
``` wherein similar shorthand notation, as elsewhere in this disclosure, has been utilized.

B. Cyclic Reversed Orientation Compounds

A "reversed" or "retro" peptide sequence as disclosed herein refers to that part of an overall sequence of covalently-bonded amino acid residues (or analogs or mimetics thereof) wherein the normal carboxyl-to-amino direction of peptide bond formation in the amino acid backbone has been reversed such that, reading in the conventional left-to-right direction, the amino portion of the peptide bond (as underlined below) precedes (rather than follows) the carbonyl portion:

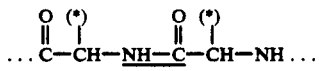

wherein "*" represents a side chain group. See, generally, Goodman, M. and M. Chorev, Accounts of Chem. Res. 12:423-430 (1979). Compounds containing such sequences are referred to herein as "reversed" peptides.

The reversed orientation peptides described herein include (a) those wherein one or more amino-terminal residues are converted to a reversed ("rev") orientation (thus yielding a second "carboxyl terminus" at the left-most portion of the molecule), and (b) those wherein one or more carboxyl-terminal residues are converted to a reversed ("rev") orientation (yielding a second "amino terminus" at the right-most portion of the molecule). It will be seen that a normal peptide (amide) bond cannot be formed at the interface between a normal orientation residue and a reverse orientation residue:

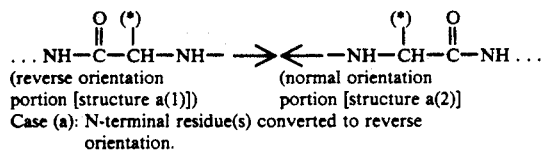
(reverse orientation portion [structure a(1)])   (normal orientation portion [structure a(2)])
Case (a): N-terminal residue(s) converted to reverse orientation.

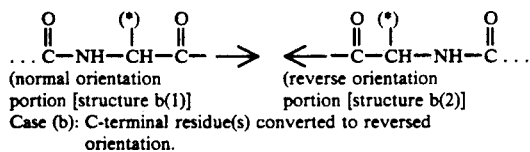
(normal orientation portion [structure b(1)])   (reverse orientation portion [structure b(2)])
Case (b): C-terminal residue(s) converted to reversed orientation.

Therefore, certain of the reversed peptide compounds of the invention can be formed by utilizing an appropriate amino acid mimetic moiety to link the two adjacent portions of the sequences depicted above utilizing a reversed peptide (reversed amide) bond. In case (a) above, a central residue of a diketo compound, as shown by moiety 3 in structure II below, may conveniently be utilized to link structures a(1) and a(2) with two amide bonds to achieve a peptidomimetic structure. In case (b) above, a central residue of a diamino compound, as shown by moiety 3 in Structure III below, will likewise be useful to link structures b(1) and b(2) with two amide bonds to form a peptidomimetic structure. With reference also to Structure I above, it will be seen that such central residues are most preferably utilized at residue position 3.

The reversed direction of bonding in such compounds will generally, in addition, require inversion of the enantiomeric configuration of the reversed amino acid residues in order to maintain a spatial orientation of side chains that is similar to that of the non-reversed peptide. The configuration of amino acids in the reversed portion of the peptides is preferably D, and the configuration of the non-reversed portion is preferably L. Opposite or mixed configurations are acceptable when appropriate to optimize a binding activity.

1. Diketo Cyclic Reversed Peptides

Thus, a second class of compounds of the invention is represented by the formula:

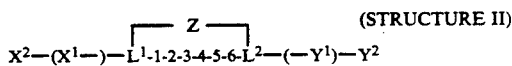

and pharmaceutically acceptable salts thereof, wherein:

$L^1$ and $L^2$ are each, or are together, a residue of an amino acid, an amino acid derivative or an amino acid mimetic having a functional group suitable for the formation of a cyclizing bridge between $L^1$ and $L^2$:

Z is a cyclizing moiety or bond between $L^1$ and $L^2$;

1 is optional, and where present, is of reversed orientation and is selected from Sar, Leu, Tyr, Phe, Ile, Pro, Gly, Ala, Val, norLeu, norVal, β-Ala, Trp, D-Nal and (Ada)-Ala;

2 is of reversed orientation and is selected from Arg, N-methylArg, homoArg, and norArg;

3 is a moiety suitable for linking reversed-orientation residue 2 with residue 4, and is preferably of the form

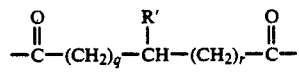

wherein q and r are independently integers of 0, 1 or 2;

4 is selected from Asp and, where Z is norArg, Glu;

5 is optional and, where present, is selected from Ser, Thr, Tyr, Trp, Ala, Val, Phe,

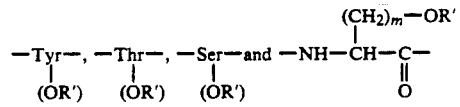

wherein m is 2, 3 or 4;

6 is optional and, where present, is selected from Pro, 3-thioPro, 1,1-ACC, Dhp, Hyp, homoPro and Phe;

$X^1$ and $Y^1$ are each optional and, where present, are independently selected from sequences of from 1 to 4 D- or L-amino acids and amino acid analogs;

$X^2$ is an optional substituent selected from $R'_2N-$(including $R'HN-$ and $H_2N-$), $R'O-$(including hydroxyl), $H_2NNH-$ and $R'S-$;

$Y^2$ is an optional carboxyl-terminal substituent selected from $-OR'$ (including hydroxyl), $-NR'_2$ (including $-NH_2$ and $-NHR'$), $-NHNH_2$ and $-SR'$;

and wherein each R' is individually a pharmaceutically suitable substituent group, preferably one selected from hydrogen, from linear and branched, unsubstituted and substituted $C_1-C_8$ lower alkyls, $C_2-C_8$ alkenyls, $C_2-C_8$ alkynyls, $C_6-C_{14}$ aryls, $C_7-C_{14}$ alkaryls, $C_7-C_{14}$ alkaryls and $C_3-C_{14}$ cycloalkyls, and, in the case of $-NR'_2$, from cyclized groups forming (in an attachment with the nitrogen atom) a 5-8 membered heterocyclic ring optionally containing oxygen, nitrogen or sulfur as a further ring heteroatom.

In the above Structure II, cyclization may generally be achieved in the manners described above for Structure I. However, it is to be noted that the orientation of peptide bonding in the compounds of Structure II is, in residues to the left of residue number 3, reversed in direction such that a carboxyl "terminus" group is exposed in residue 2 or, if present, residue 1, rather than an amino group. Therefore, linking groups in position $L^1$ may utilize for bonding to this carboxyl terminus an amino moiety, as for example a diamino moiety such as those in preferred structures of the form —NH—(CH$_2$)$_t$—NH— wherein t is 1, 2 or 3, which can simultaneously provide as (L$^2$) a second amino moiety for cyclizing bonding to the normal-orientation carboxyl terminus of residue number 4 or, if present, 5 or 6.

Other forms of linking groups, including Z groups, and various combination of bonding between terminal functional groups and side chain function groups on L$^1$ and L$^2$, will be recognized by those skilled in the art in view of the present disclosure. In particular, the discussion above with respect to use of amino acid analogs and amino acid mimetic structures is applicable also here.

Residues L$^1$, 1, 2 and Y$^1$ are preferably D-amino acids. Residue 1 in Structure II is most preferably absent or Sar, and is secondarily preferred to be D-forms of Leu, Tyr or Gly; residue 2 is most preferably Arg (particularly D-Arg); in residue 3, q and r are most preferably zero and R' is most preferably hydrogen, with lower alkyl also being preferred; residue 4 is most preferably Asp; residue 5 is most preferably Ser; and residue 6 is most preferably Pro. The sequence Sar$_{rev}$—D—Arg$_{rev}$—C(=O)—CH$_2$—C(=O)—Asp—Ser—Pro, wherein the subscript "rev" indicates a reverse-form residue, is especially preferred for residues 1-2-3-4-5-6.

As with Structure I, X$^1$ and Y$^1$ are both optional, and are selected from the same constituents as those of X$^1$ and Y$^1$ of Structure I (with appropriate utilization of reversed orientation residues in X$^1$). Optional substituent X$^2$ is of a form suitable for bonding to, typically, a carboxyl terminus on X$^1$ or L$^1$.

For group 3 in Structure II, an especially preferred residue is

—C(=O)—(CH$_2$)$_s$—C(=O)— wherein s is an integer of from 1 to about 5, preferably 1 to 3, and most preferably 1.

A particularly preferred compound class of Structure II is:

X$^2$—X$_{rev}^1$—L$_{rev}^1$—Arg$_{rev}$—C(=O)—CH$_2$—C(=O)—Asp—Ser—Pro—L$^2$—Y$^1$—Y$^2$ wherein R' in X$^1$ and Y$^1$ is preferably hydrogen or lower alkyl.

Specifically preferred compounds include:

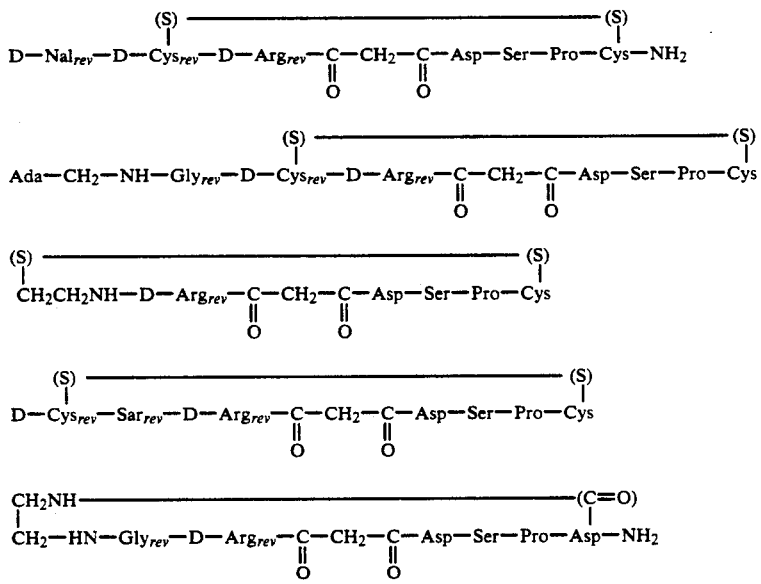

As with Structure I, derivatives of the peptides of Structure II may be useful in the generation of antigens which, in turn, may be useful to generate antibodies. These antibodies will in some cases themselves be effective in inhibiting cell adhesion or modulating immune activity by acting as receptors for matrix proteins or other ligands, or, if anti-idiotypic, by acting to block cellular receptors.

2. Diamino Cyclic Reversed Compounds

The compounds of class III of the invention are represented by the formula:

X$^2$—(X$^1$—)L$^1$-1-2-3-4-5-6-L$^2$(—Y$^1$)—Y$^2$    (STRUCTURE III)

with Z bridging L$^1$ and L$^2$.

and pharmaceutically acceptable salts thereof, wherein:

L$^1$ and L$^2$ are each, or are together, a residue of an amino acid, an amino acid derivative or an amino acid mimetic having a functional group suitable for the formation of a cyclizing bridge between $L^1$ and $L^2$;

Z is a cyclizing moiety between $L^1$ and $L^2$;

1 is optional and, where present, is selected from Leu, Tyr, Phe, Ile, Pro, Gly, Ala, Val, norLeu, norVal, β-Ala, Trp, Nal, (Ada)-Ala and Sar;

2 is selected from Arg, N-methylArg, homoArg, and norArg;

3 is a moiety suitable for linking residue 2 with reversed-orientation residue 4, and is preferably of the form $$-NH-(CH_2)_q-\underset{\underset{R'}{|}}{CH}-(CH_2)_r-NH-$$

wherein q and r are independently integers of 0, 1 or 2;

4 is of reversed orientation and is selected from Asp and, where 2 is norArg, Glu;

5 is optional and, where present, is of reversed orientation and is selected from Ser, Thr, Tyr, Trp, Ala, Val, Phe, $$-Tyr-,\ -Thr-,\ -Ser-\text{ and }-NH-\underset{\underset{O}{\|}}{\overset{\overset{(CH_2)_m-OR'}{|}}{C}}$$
$$\ \ \ \ |\ \ \ \ \ \ \ \ \ \ |\ \ \ \ \ \ \ \ \ |$$
$$\ \ (OR')\ \ (OR')\ \ (OR')$$

wherein m is 2, 3 or 4;

6 is optional and, where present, is of reversed orientation and is selected from Pro, 3-thioPro, 1,1-ACC, Dhp, Hyp, homoPro and Phe;

$X^1$ and $Y^1$ are each optional and, where present, are independently selected from 1 to 4 D- or L-amino acids and amino acid analogs;

$X^2$ is an optional $N^\alpha$-substituent selected from R' (including hydrogen) and R'CO—;

$Y^2$ is an optional substituent selected from —R' (including hydrogen) and —COR';

and wherein each R' is individually a pharmaceutically suitable substituent group, preferably one selected from hydrogen, from linear and branched, unsubstituted and substituted $C_1$-$C_8$-lower alkyls, $C_2$-$C_8$ alkenyls, $C_2$-$C_8$ alkynyls, $C_6$-$C_{14}$ aryls, $C_7$-$C_{14}$ alkaryls, $C_7$-$C_{14}$ alkaryls and $C_3$-$C_{14}$ cycloalkyls, and, in the case of —$NR'_2$, from cyclized groups forming (in an attachment with the nitrogen atom) a 5-8 membered heterocyclic ring optionally containing oxygen, nitrogen or sulfur as a further ring heteroatom.

In the above Structure III, cyclization may generally be achieved in the manners described above with respect to Structures I and II. Further, it will be seen that the right-most "terminus" exposed by residue number 4 (or, if present, 5 or 6) is an amino moiety rather than the carboxyl moiety of a non-reverse-orientation sequence, and that a linking group $L^1$ bearing a carboxyl group and suitable for forming an amide bond with this right-most terminus will be appropriate. Such structures include those of the form $$-\underset{\underset{O}{\|}}{C}-(CH_2)_q-\underset{\underset{R'}{|}}{CH}-(CH_2)_r-\underset{\underset{O}{\|}}{C}-$$

q and r are as defined above; such a structure can, in view of its second carboxyl group, also serve as $L^1$ by bonding to the amino terminus of residue number 2 or, if present, residue 1. Other forms of linking groups $L^1$ and $L^2$, and Z groups, will be recognized in view, for example, of the discussion above with respect to Structures I and II. $L^2$ may in such a case be selected from des-α-aminoCys and PMP.

For group 3 in Structure III, an especially preferred residue is —HN—$(CH_2)_s$—NH—, wherein s is an integer of from 1 to about 5, preferably 1 to 3, and most preferably 1.

Residues 4, 5, 6, $L^2$ and $Y^1$ in Structure III are preferably D-amino acids. Residue 1 in Structure III is most preferably absent or Sar and is secondarily preferred to be Leu, Tyr or Gly; residue 2 is most preferably Arg; in residue 3, q and r are most preferably zero and R' is most preferably hydrogen, with lower alkyl also being preferred; residue 4 is most preferably D-Asp, residue 5 is most preferably D-Ser, residue 6 is preferably D-Pro. The sequence Sar-Arg-NH-$(CH_2)_t$-NH-D-Asp-D-Ser-D-Pro, where t is 1, 2 or 3, is most preferred for residues 1-2-3-4-5-6.

As with Structures I and II, $X^1$ and $Y^1$ are both optional, and are selected from the same constituents as those of $X^1$ and $Y^1$ of Structures I and II (with appropriate consideration of reversed orientation residues in $Y^1$). Optional substituent $Y^2$ is of a form suitable for bonding to, typically, an amino terminus on $Y^1$ or $L^2$.

A particularly preferred compound of Structure III is:

$$X^2-X^1-L^1-Arg-NH-\underset{\underset{R'}{|}}{CH}-NH-D-Asp_{rev}-D-Ser_{rev}-D-Pro_{rev}-L^2-Y^1-Y^2$$

More specifically, preferred compounds are:

(Ada)—Ac—Gly—Cys$^{(S)}$—Arg—NH—CH$_2$NH—D—Asp$_{rev}$—D—Ser$_{rev}$—D—Pro$_{rev}$—D—Cys$_{rev}^{(S)}$ D—Nal—Cys$^{(S)}$—Arg—NH—CH$_2$—NH—D—Asp$_{rev}$—D—Ser$_{rev}$—D—Pro$_{rev}$—D—Cys$_{rev}^{(S)}$—NH$_2$ Mpr$^{(S)}$—Arg—NH—CH$_2$—NH—D—Asp$_{rev}$—D—Ser$_{rev}$—D—Pro$_{rev}$—D—Cys$_{rev}^{(S)}$ -continued

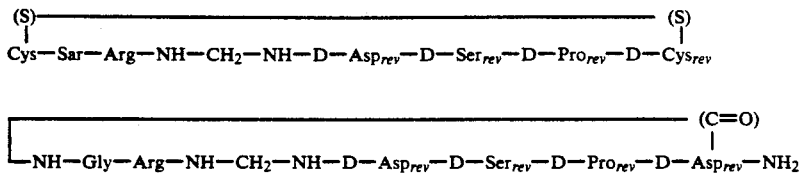

As with Structures I and II, derivatives of the peptides of Structure III may be useful in the generation of antigens which, in turn, may be useful to generate antibodies. These antibodies will, in some cases, themselves be effective in inhibiting cell adhesion or modulating immune activity by acting as receptors for matrix proteins or other ligands or, if anti-idiotypic, by acting to block cellular receptors.

NON-GLYCINE-CONTAINING CYCLIC COMPOUNDS

Compounds of this class containing, for example, the sequence RCD were synthesized and found to be effective in modulating cell adhesion activity. This demonstrates that the residue glycine is not necessary to adhesion modulation activity and that residues such as cysteine may replace glycine in the peptide while maintaining activity. Moreover, it is an aspect of the invention that cysteine or other cyclizing residues are able in this regard to facilitate cyclization via disulfide or other side chain bridging.

The compounds of Class IV of the invention are represented by the formula:

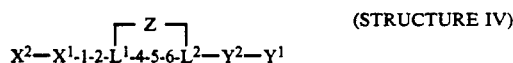
(STRUCTURE IV)

and pharmaceutically acceptable salts thereof, wherein $L^1$ and $L^2$ are each, or are together, a residue of an amino acid, an amino acid analog or an amino acid mimetic having a functional group suitable for the formation of a cyclizing bridge between $L^1$ and $L^2$;

Z is a cyclizing moiety or bond between $L^1$ and $L^2$;

1 is optional and, where present, is selected from Leu, Sar, D-Nal, Tyr, Phe, Ile, Pro, Gly, Ala, Val, norLeu, norVal, β-Ala, Trp, and (Ada)-Ala;

2 is selected from Arg, N-methylArg, homoArg and norArg.

4 is selected from Asp and, where 2 is norArg, Glu.

5 is optional and, where present, is selected from Ser, Thr, Tyr, Trp, Ala, Val, Phe,

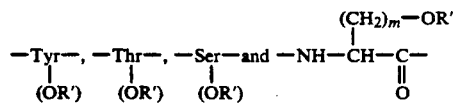

wherein m is 2, 3 or 4;

6 is optional and, where present, is selected from Pro, 3-thioPro, 1,1-ACC, Dhp, Hyp, homoPro and Phe;

$X^1$ and $Y^1$ are each optional and, where present, are independently selected from sequences of 1 to 4 D- or L-amino acids or amino acid analogs;

$X^2$ is an optional $N^\alpha$-substituent selected from R′-(including hydrogen) and R′CO—; and $Y^2$ is an optional carboxyl-terminal substituent selected from —OR′ (including hydroxyl), —NR′$_2$ (including —NH$_2$ and —NHR′), —NHNH$_2$ and —SR′;

and wherein each R′ is individually a pharmaceutically suitable substituent group, preferably one selected from hydrogen, from linear and branched, unsubstituted and substituted $C_1$-$C_8$ lower alkyls, $C_2$-$C_8$ alkenyls, $C_2$-$C_8$ alkynyls, $C_6$-$C_{14}$ aryls, $C_7$-$C_{14}$ alkaryls, $C_7$-$C_{14}$ alkaryls and $C_3$-$C_{14}$ cycloalkyls, and, in the case of —NR′$_2$, from cyclized groups forming (in an attachment with the nitrogen atom) a 5-8 membered heterocyclic ring optionally containing oxygen, nitrogen or sulfur as a further ring heteroatom.

It is particularly preferred that residue number 1 be absent or Leu; that residue 2 be Arg; that residue $L^1$ be Cys; that residue 4 be Asp; that residue 5 be absent or Ser; that residue 6 be absent or Pro; and that residue $L^2$ be Cys. Thus, the structures Leu-Arg-Cys-Asp-Ser-Pro-Cys,
Arg-Cys-Asp-Ser-Pro-Cys, and
Arg-Cys-Asp-Pro-Cys are particularly preferred for residues 1-2-$L^1$-4-5-6-$L^2$. The compounds

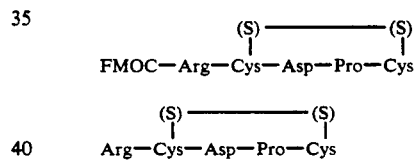

are particularly preferred.

As discussed above in conjunction with Structure I, linking residues $L^1$ and $L^2$ other than Cys, and Z groups other than simple bonds, may also be usefully employed in the context of Structure IV. It will be seen in this regard that the presence of residue numbers 2 and 4 on either side of $L^1$ will typically require cyclization (through Z) to $L^2$ through a side chain or other functional group on $L^1$ that is not engaged in bonding to residues 2 or 4. Residue $L^2$ may more generally be engaged in cyclization through either a terminal (typically, carboxyl) functional group or a side chain functional group.

As noted generally above with respect to $X^2$ and $Y^2$ substituents, acyl and amino groups derived from bulky substituents such as adamantaneacetic acid, 2-naphthylacetic acid, 2-norbornaneacetic acid, 3-noradamantanecarboxylic acid, and 1- or 2- adamantylamine are among the preferred substituents.

As with Structures I, II and III, derivatives of the peptides of Structure IV may be useful in the generation of antigens which, in turn, may be useful to generate antibodies. These antibodies will, in some cases, themselves be effective in inhibiting cell adhesion or modulating immune activity by acting as receptors for matrix proteins or other ligands or, if anti-idiotypic, by acting to block cellular receptors.

Examples

Although any methods and materials similar or equivalent to those described herein can be used in the practice or testing of the present invention, the preferred methods and materials are now described. As set forth above, all publications to which reference is made are incorporated herein by reference.

1. Synthesis and Formulation of Compounds

The "backbones," i.e., the peptide-bond linked portions of the cyclic compounds of the invention were generally synthesized using solid phase peptide synthesis, and then cyclized using a procedure which, where necessary, selectively removed protective groups from only the residues involved in cyclizing. In this way, the peptide sequence in the compound was not changed or lengthened, but the peptide was properly cyclized. Other methods for synthesis and cyclization are known in the art and may be employed in the preparation of the cyclic compounds and formulations disclosed herein.

Thus, peptide sequences in the compounds of this invention may be synthesized by the solid phase peptide synthesis (for example, BOC or FMOC) method, by solution phase synthesis, or by other techniques known in the art including combinations of the foregoing methods. The BOC and FMOC methods, which are established and widely used, are described in the following references:

Merrifield, J. Am.Chem.Soc., 85: 2149–2154 (1963);

Meienhofer, in: *Hormonal Proteins and Peptides*, Vol. 2 C.H. Li, Ed., pp. 48–267 (Academic Press, 1983);

Barany and Merrifield, in: *The Peptides*, Vol.2, E.- Gross and J. Meienhofer, Eds., pp. 3–285 (Academic Press, New York, 1980);

In the preferred solid phase synthesis method, a peptide of a desired length and sequence is produced through the stepwise addition of amino acids to a growing peptide chain which is covalently bound to a solid resin particle. Automated synthesis may be employed in this method.

In the preferred application of this method the C-terminal end of the growing peptide chain is covalently bound to a resin particle and amino acids having protected α-amino groups are added in the stepwise manner indicated above. A preferred α-amino protecting group is the tertbutyloxycarbonyl (BOC) group, which is stable to the condensation conditions and yet is readily removable without destruction of the peptide bonds or racemization of chiral centers in the peptide chain. At the end of the procedure the product peptide is cleaved from the resin, and any remaining protecting groups are removed by treatment under acidic conditions such as, for example, with a mixture of hydrobromic acid and trifluoroacetic acid, with trifluoromethane sulfonic acid or with liquified hydrofluoric acid. For the present cyclic peptides, hydrofluoric acid was typically used.

The preferred steps for solid phase peptide synthesis using the symmetric anhydride method are shown in Table 1, below. The preferred steps for solid phase peptide synthesis using the active ester method are shown in Table 2, below. The preferred steps using the DCC method are shown in Table 3, below.

TABLE 1

Solid Phase Peptide Synthesis (symmetrical anhydride method)

| Step | Reagent | Vol.* (ml) | Time (min) |
|---|---|---|---|
| 1 | DCM wash (3 times) | 15 | 1 (per wash) |
| 2 | TFA-DCM | 15 | 1.5 |
| 3 | TFA-DCM | 15 | 30 |
| 4 | DCM wash (6 times) | 15 | 1 (per wash) |
| 5 | TEA-DCM | 15 | 1.5 |
| 6 | DCM wash (6 times) | 15 | 1 (per wash) |
| 7 | Symmetrical anhydride (0.8 meq) of BOC-amino acid in DCM | 10 | 120 or until monitoring shows complete reaction |
| 8 | Recouple if necessary by repeating Steps 4–7 | | |
| 9 | DCM wash (3 times) | 15 | 1 (per wash) |

*The volume given is for synthesis using 0.4 meq. of growing peptide chain on 1 gram of resin.

TABLE 2

Solid Phase Peptide Synthesis (active ester method)

| Step | Reagent | Vol* (ml) | Time (min) |
|---|---|---|---|
| 1 | DCM wash (3 times) | 15 | 1 (per wash) |
| 2 | TFA-DCM | 15 | 1.5 |
| 3 | TFA-DCM | 15 | 30 |
| 4 | DCM-wash (6 times) | 15 | 1 (per wash) |
| 5 | DIEA-DCM (2 times) | 15 | 1.5 (per wash) |
| 6 | DCM wash (6 times) | 15 | 1 (per wash) |
| 7 | DMF wash (3 times) | 15 | 1 (per wash) |
| 8 | BOC-amino acid active ester (0.8 meq) in DMF | 7 | 2 hr or until monitoring shows complete reaction |
| 9 | Recouple if necessary by repeating Steps 4–9 | | |
| 10 | DMF wash (6 times) | 15 | 1 (per wash) |
| 11 | DCM wash (3 times) | 15 | 1 (per wash) |

*The volume given is for the synthesis using 0.4 meq. of growing peptide chain on one gram of resin.

TABLE 3

Solid Phase Peptide Synthesis (DCC method)

| Step | Reagent | Vol* (ml) | Time (min) |
|---|---|---|---|
| 1 | DCM wash (3 times) | 15 | 1 (per wash) |
| 2 | 50% TFA-DCM | 15 | 1 |
| 3 | 50% TFA-DCM | 15 | 20 |
| 4 | DCM wash (3 times) | 15 | 1 |
| 5 | IPA wash (2 times) | 15 | 1 |
| 6 | DCM wash (3 times) | 15 | 1 |
| 7 | 10% TEA-DCM | 15 | 1 |
| 8 | 10% TEA-DCM | 15 | 5 |
| 9 | DCM wash (4 times) | 15 | 1 (per wash) |
| 10 | BOC AA (1.2 meq.) in DCM (or DMF) | | 120 |
| 11 | DCC (1.2 meq., 0.5 M) in DCM | | |
| 12 | Recouple if necessary by repeating steps 4–11 | | |
| 13 | DCM wash (2 times) | 15 | 1 (per wash) |
| 14 | 50% CH$_3$OH—DCM wash | 15 | 1 |
| 15 | DCM wash (3 times) | 15 | 1 (per wash) |
| 16 | IPA wash (3 times) | 15 | 1 (per wash) |
| 17 | DCM wash (3 times) | 15 | 1 (per wash) |

*The volume given is for the synthesis using 0.6 meq. of growing peptide chain on one gram of resin.

Alternatively, peptide sequences or portions thereof may be synthesized in solution. See, e.g., M. Mutter and E. Bayer, "The Liquid Phase Method for Peptide Synthesis" in: *The Peptides*, E. Gross and J. Meienhofer, Eds., pp. 285–332, Academic Press (1980), for one example of peptide synthesis in solution.

General strategies for preparing cyclic compounds of the invention typically involve selective protection of side chains or termini so that cyclization may be accomplished. Essentially, the peptide bond linked linear backbone of the compound is wholly or partially constructed using one type of protection means on potentially reactive groups (e.g., side groups) on residues not involved in cyclization, with the residues bearing functional groups to be cyclized being protected with another type ("orthogonol protection"). The moieties to be cyclized are then chemically revealed without disturbing the other protective groups. The revealed moieties are then appropriately activated and cyclized. Following this, the remainder of the peptide bond linked portion of the compound is completed (if the partial backbone was cyclized), deprotected, cleaved from the resin (when appropriate) and purified. In this way, functional groups not intended for cyclization are not prematurely exposed and cyclization occurs in the proper location.

For example, a peptide may be synthesized on a resin using FMOC protection on the side chains, or on the terminus or other portion, which will be used for cyclization. Preferred steps for solid phase peptide synthesis using such FMOC orthogonal protection are set forth in Table 4 below. The remainder of the potentially reactive groups of the peptide may be BOC protected. Upon cyclization, the FMOC-protected side chain/termini are deprotected, without deprotection of the BOC-protected moieties. Inappropriate cyclization or other modification is thereby prevented. If cyclization is to be performed prior to completion of the backbone construction, the temporary terminus should be blocked with a protecting group stable to the deprotection and cyclization conditions for the involved cyclized functional groups. Following cyclization, the temporary terminus is then deprotected and the peptide construction is completed.

TABLE 4

| | Solid Phase Peptide Synthesis (FMOC method) | | |
|---|---|---|---|
| Step | Reagent | Vol* (ml) | Time (min) |
| 1 | DCM wash (2 times) | 15 | 1 (per wash) |
| 2 | DMF wash (2 times) | 15 | 1 (per wash) |
| 3 | Deprotect: DMF: piperidine (4:1) | 15 | 20 |
| 4 | DMF wash (4 times) | 15 | 1 (per wash) |
| 5 | DCM wash (3 times) | 15 | 1 (per wash) |
| 6 | Symmetrical anhydride of FMOC amino acid in DCM (or DMF:DCM) (with 2-3 fold equivalent excess of anhydride) | 15 | 15 |
| 7 | Add 1.0 mL of 10% DIEA in DCM | 1 | 15 or until monitoring shows coupling complete |
| 8 | Recouple if necessary by repeating steps 5-7 | | |
| 9 | DMF wash (5 times) | 15 | 1 (per wash) |
| 10 | IPA wash (5 times) | 15 | 1 (per wash) |
| 11 | DCM wash (5 times) | 15 | 1 (per wash) |

*The volume given is for synthesis using 0.4 meq. growing peptide chain on one gram of resin.

The compounds after cleavage from the resin are isolated and purified by means well known in the art. For example, the cleaved compound/resin mixture is washed in turn with several portions of diethyl ether and then extracted with several portions of aqueous acetic acid. The resin may then be discarded. The aqueous acetic acid extracts are combined, concentrated, resuspended in water and lyophilized. Following this, the crude compound can be purified by reversed phase high pressure liquid chromatography (HPLC), or by size exclusion chromatography, partition chromatography on polysaccharide gel media such as Sephadex G10 or G25, or counter current distribution.

The composition of the final compound may be confirmed by amino acid analysis after degradation of the compound by standard means, by amino acid sequencing techniques, or by FAB-MS techniques. For the examples herein, compounds were usually purified by reverse-phase HPLC and subjected to amino acid analysis.

One important aspect in final purification is the removal of fluoride. Even small amounts of fluoride may alter the biological profile of the peptides. Generally, ion exchange chromatography, using $AG_3$-4X acetate for example, to exchange the fluoride salt, is used. The subject compound is dissolved in water and passed over an acetate-form resin. The eluate is collected, and lyophilized to dryness. One skilled in the art will recognize that in some cases, such as, for example, where fluoride is removed through reverse-phase chromatography, or other methods, or where FMOC protection has been utilized without HF cleavage, fluoride removal using ion exchange chromatography is unnecessary.

Salts of carboxyl groups of the product compounds may be prepared in the usual manner by contacting the compound with one or more equivalents of a desired base such as, for example, a metallic hydroxide base such as, for example, sodium hydroxide; a metal carbonate or bicarbonate base such as, for example, sodium carbonate or sodium bicarbonate; or an amine base such as, for example, triethylamine, triethanolamine, and the like. In all such procedures and in other synthetic procedures provided herein, the pH should be kept below approximately 8 in order to avoid complications such as racemization, deamidation, peptide degradation or other undesirable side reactions.

Acid salts of the compounds may be prepared by contacting the polypeptide with one or more equivalents of the desired inorganic or organic acid, such as, for example, hydrochloric acid, acetic acid or citric acid.

Esters of carboxyl groups of the compounds may be prepared by any of the usual means known in the art for converting a carboxylic acid or precursor to an ester. One preferred method for preparing esters of the present compounds, when using the Merrifield synthesis technique described above, is to cleave the completed peptide sequence from the resin in the presence of the desired alcohol either under basic or acidic conditions, depending upon the resin. Thus the C-terminal end of the peptide when freed from the resin is directly esterified without isolation of the free acid. Alternatively, especially where the desired compound contains one or more glutamic acid or aspartic acid residues, C-terminal amino acid esters may be made using solution phase synthesis wherein the C-terminal residue bearing the desired ester functionality is incorporated.

Amides of the compounds of the present invention may also be prepared by techniques well known in the art for converting a carboxylic acid group or precursor to an amide. A preferred method for amide formation at the C-terminal carboxyl group is to synthesize the peptides by solid phase methods on an appropriate resin, for example a 4-methylbenzhydrylamine or a benzhydrylamine resin, and thereafter to cleave the polypeptide from a solid support with an appropriate acid. If the desired amide is to include a secondary or tertiary amino group, then the amide may be synthesized using solution phase techniques wherein an aminated C-terminal residue bearing the desired amide functionality is incorporated.

N-Acyl derivatives of an amino group of the present peptides may be prepared by utilizing an N-acyl protected amino acid for the final condensation, or by acylating a protected or unprotected functional group in the compound. Acylation may be carried out using standard acylating reagents such as acyl halides, anhydrides, acyl imidazoles, and the like prior to deprotection of the residue side chains.

The coupling reaction is generally carried out at 0°–25° C., deprotection at room temperature, and cleavage at a reduced temperature of −5° to 0° C. (especially with HF cleavage). The exact temperature for any particular reaction will, of course, be dependent upon the substrates, reagents, solvents and so forth, all being well within the skill of the practitioner. Illustrative reaction conditions for these processes may be gleaned from the examples.

The compounds of this invention may also be synthesized using any techniques that are known to those in the synthetic arts, for example, those described in HoubenWeyl, Methoden Der Organischen Chemie, Vol. 15-II, pg. 1–806 (1974), Georg-Thieme-Verlag, Stuttgart, or by recombinant DNA technology.

Presented below are examples wherein cyclization of the present compounds is achieved with a disulfide linkage between side chain sulfur atoms. Example 1 relates general procedures as applied to two representative RGD-containing peptides, while Examples 2 and 3 give procedures for preparing disulfide linked compounds according to Structures II and III above.

EXAMPLE 1

General Procedure for Synthesis of Disulfide Linked Cyclic Compounds

Peptides of this class were synthesized and cyclized as the disulfide. Such peptides include:

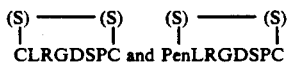

CLRGDSPC and PenLRGDSPC experimental details for which follow.

All t-butyloxycarbonyl protected amino acids with chiral centers were of the L-configuration. Such protected amino acids included the t-butyloxycarbonyl derivatives of Ser(O-benzyl), Asp(β-cyclohexyl ester), Arg(tosyl), Cys(S-p-methylbenzyl) and Pen(S-p-methoxybenzyl).

Peptide synthesis. Stepwise build up of the peptides depicted above on the BOC-Cys(S-p-methylbenzyl)-Merrifield resin was done automatically on a Beckman 990C peptide synthesizer (Beckman Instrument Company, Palo Alto, Calif. 94304) and using 2 equivalents of protected amino acids for each equivalent of peptide on-resin. Automated synthesis was performed according to the general procedures published with the synthesizer.

Trifluoroacetic acid (50% in DCM) was used for deblocking. Triethyl amine (10% in DCM) was used for neutralization. Resin washing was accomplished by application of MeOH-DCM (50:50), isopropyl alcohol and methylene chloride at the other steps. Couplings (usually 120 minutes per coupling) were mediated by N,N'-dicyclohexylcarbodiimide (DCC) in either DCM, DMF, or mixtures thereof depending on the solubility of the respective amino acid residue being coupled.

The coupled peptides were cleaved from the peptide resin by treatment with distilled anhydrous HF (10 ml/g peptide resin) in the presence of anisole (1 ml/g peptide resin) and dimethyl sulfide (0.5 ml/g) as scavengers. The reaction was carried out at −5° C. for one hour. After removal of the HF under reduced pressure, the resin was washed three times with diethyl ether. The peptide was extracted from the resin with 1N acetic acid and then lyophilized.

Cyclization to the Disulfide Using Iodine. Approximately 2 grams of the respective cleaved peptides were dissolved in 500 ml 80% acetic acid. While the solution was stirring, a solution of $I_2$, at a 10-fold molar excess over peptide, in glacial acetic acid was added dropwise over 30 minutes. The mixture was stirred for another hour. After this, ascorbic acid was added until the reddish solution turned colorless. The solution was then concentrated by evaporation (Rotavap, Buchi Corporation), and the residue redissolved in water. The aqueous solution was then lyophilized.

Purification. The crude Cyclic peptide was purified using preparative RP-HPLC (Waters Delta Prep 3000, Millipore Corporation, Millford, Mass.) according to the manufacturer's general instructions. The gradient (Triethylaminephosphate (TEAP, pH 2.2–2.4)/acetonitrile 100/0 to 79/21) was applied over 30 minutes at 90 ml/min. The fractions were analyzed by Beckman RP-C18 columns (Beckman Instrument Company, Palo Alto, Calif. 94304) and the fractions containing the desired cyclic peptide were pooled. Desalting of the pooled fractions was carried out on a RP-HPLC column using a 0.5% aqueous acetic acid acetonitrile gradient from 100/0 to 79/21 over 30 minutes at 90 ml/min. The peptides were then dissolved in water, and fluoride was removed via ion exchange chromatography as described above if necessary. Highly purified fractions were pooled and lyophilized.

EXAMPLE 2

Synthesis of Disulfide Linked, Diamino Cyclic Reversed Peptides

In this example, the following peptide is synthesized:

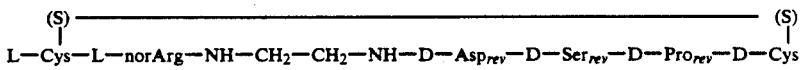

Solution phase BOC and FMOC methods are used in this synthesis. The product from each step prior to HF cleavage is purified by silica gel chromatography. The general approach is to synthesize the reversed form of the peptide and attach it to the partially protected diaminopropane moiety, followed with coupling amino acids in the normal orientation to the deprotected diaminopropane coupled to the reversed peptide segment.

The peptide is then deprotected with HF, the resulting crude dicysteine containing product cyclized, and the disulfide compound purified.

N-BOC-D-aspartic acid is protected with α-9-fluorenylmethyl ester, and the β-cyclohexyl ester is N-deprotected with 1:1 TFA/DCM. The resulting ammonium trifluoroacetate is coupled to N-BOC-O-benzyl-D-serine (1.05 eq.) using benzotriazol-1-yloxy-tris(-dimethylamino)phosphonium hexafluorophosphate (BOP reagent, 1.2 meq.), 1-hydroxybenzotriazole hydrate (HOBt, 0.12 meq.), and diisopropylethylamine (DIEA, 4 meq.) in DMF. This dipeptide product is N-deprotected and coupled as above sequentially to N-BOC-D-proline and N-BOC-S-4-methylbenzyl-D-cysteine. The OFm ester of the aspartic acid residue is deprotected with 20% piperdine/DMF and the free carboxylate product coupled to 1-(9-fluorenylmethyl-carboxamide)-2-aminoethane with BOP activation. The product of this reaction is coupled sequentially to N-α-FMOC-Ng-tosyl-L-(nor)arginine and N-BOC-S-4-methylbenzyl-L-cysteine, using 20% piperidine/DMF deprotection and activation with BOP. After a final deprotection with HF, the resulting cysteine sulfhydryls are cyclized in an iodine oxidation procedure to produce the final product depicted above.

EXAMPLE 3

Synthesis of Disulfide Linked, Diketo Cyclic Reversed Peptides

In this example, the following peptide is synthesized:

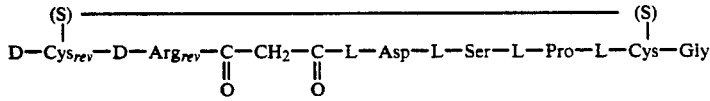

Solution phase BOC and FMOC methods are used in this synthesis. The product from each step prior to HF cleavage is purified by silica gel chromatography. As can be seen, this peptide contains reversed (rev) forms of D-Cys and D-Arg. The general approach is to synthesize the L-configuration segment of the peptide and then attach, through an amide bond, a residue of malonic acid mono-t-butyl ester. The synthesis is then continued by coupling amino acids in the reversed orientation to the deprotected malonate. The compound is then deprotected with HF, the resulting crude dicysteine-containing product cyclized and the disulfide compound purified.

BOC-Gly(O-benzyl) ester is N-deprotected with 1:1 trifluoroacetic acid/methylene chloride. The resulting ammonium trifluoroacetate is coupled to N-BOC-S-4-methylbenzyl-L-cysteine (1.05 eq.) using benzotriazol-1-yloxytris(dimethylamino)-phosphonium hexafluorosphosphate (BOP reagent, 1.2 eq.), 1-hydroxybenzotriazole hydrate (HOBt, 0.12 eq.), and diisopropylethylamine (DIEA, 4 eq.) in dimethylformamide (DMF).

This dipeptide product is N-deprotected and coupled as above sequentially to the following compounds: N-BOC-L-proline, N-BOC-O-benzyl-L-serine, N-BOC-(β-cyclohexyl ester)-L-aspartic acid, and malonic acid mono-t-butyl ester.

The t-butyl ester of the malonate is deprotected with 1:1 TFA/DCM and the freed carboxylate product is activated (using the BOP coupling procedure described above) and coupled to Ng-tosyl-D-arginine, t-butyl ester (free Nα-amine). The t-butyl ester of the resulting arginine-containing product is deprotected with 1:1 TFA/DCM and the free carboxylate product is again activated and coupled to S-4-methylbenzyl-D-cysteine with BOP reagent.

The product of this reaction is deprotected first with 1:1 TFA/DCM and then treated with HF, and the resulting cysteine sulfhydryls are cyclized using the iodine oxidation procedure to produce the compound depicted above.

Presented below are examples of peptides which were cyclized using an amide bridge. Example 4 is of a side chain-to-side chain amide bridge wherein the δ-carboxyl group of Glu was condensed with the ε-amino group of Lys. Example 5 is of a side chain-to-backbone amide bridge wherein the terminal α-amino group of Gly was condensed with the β-carboxyl group of Asp. In both of these examples, the amino acid backbone was fully assembled, and then cyclized, on a resin.

Example 6 shows cyclization using an amide bridge as an intermediate step. The amino acid backbone is partially assembled and then cyclized using an amide bridge. After assembly of the amide bridge, the amino acid chain is completed.

EXAMPLE 4

Synthesis of Amide Linked Cyclic Compounds (Side Chain-Side Chain Linkage)

In this example, the following compound was synthesized:

All amino acids and amino acid derivatives were purchased from BACHEM (Torrance, Calif.). 9-Fluorenylmethanol and DCC were obtained from Sigma Chemical Co. (St. Louis, Mo.). Diisopropylethylamine and 4-(dimethylamino)-pyridine were obtained from Aldrich (Milwaukee, Wisconsin). Unless otherwise noted, other reagents were of analytical grade and used without further purification.

All residues were linked by the solid phase method using BOC protection. The side chain carboxyl groups of Asp and Glu were protected as fluorenylmethyl esters and the ε-amino group of Lys and α-amino group of Gly were protected as N-FMOC. The amide bridge between the two side chains (on Glu and Lys) was synthesized while the peptide was bound on the resin. This procedure is represented by FIG. 1a.

(a) Preparation of N-BOC-O-9-fluorenylmethyl omegaesters of aspartic and glutamic acids.

The N-BOC-O-9-fluorenylmethyl omega-esters of aspartic and glutamic acids were prepared following the procedure as generally described by R. Bolin, C. T. Wang, and A.M. Felix (Organic Preparations and Procedures Intern. 21:1, pp. 67-74, 1989) with certain modifications.

N-BOC-O$^\beta$-9-fluorenylmethyl aspartate. 8.31 g (25.7 mmol) of N-BOC-O$^\alpha$-benzyl-aspartate and 4.80 g (24.5 mmol) of 9-fluorenylmethanol were dissolved in 150 ml DCM. The solution was chilled in an ice bath. 30 mg (0.24 mmol) of 4-(dimethylamino)pyridine was added to the solution followed by addition of 5.31 g (25.7 mmol) DCC in portions, over 10 minutes. The resulting mixture was stirred for one hour with continued cooling. The precipitated N,N'-dicyclohexylurea was removed by filtration and the filtrate was diluted with 250 ml DCM. This solution was extracted with (in order) 10% citric acid (2×50 ml), H$_2$O (1×50 ml), 2.5% NaHCO$_3$ (2×50 ml), H$_2$O (1×50 ml), brine (1×50 ml). The solution was then dried over MgSO$_4$, and concentrated to an oily residue. Recrystallization from methanol/ether/petroleum ether (1:3:10) yielded 10.85 g (84%) N-BOC-O$^\alpha$-benzyl-O$^\beta$-fluorenylmethyl-aspartate, with a melting point of 74°–77° C.

5.5 g (10.9 mmol) of the above product was then dissolved in 150 ml warmed methanol, and hydrogenated over 300 mg of 20% Pd(OH)$_2$/C for 1.5 hr at room temperature and a pressure of 35-40 psi. The catalyst was filtered off and the solvent was evaporated in vacuo. The residual oil was redissolved in 200 ml diethyl ether and extracted with (in order) 1% NaHCO$_3$ (3×50 ml), H$_2$O (1×50 ml), 5% citric acid (2×50 ml), and brine (1×50 ml). The ether layer was dried over MgSO$_4$ and concentrated. Recrystallization from diethyl ether/petroleum ether yielded 3.53 g of N-BOC-O$^\beta$-9-fluorenylmethyl aspartate, with a melting point of 135°–137° C.

N-BOC-O-fluorenylmethyl-glutamate (gamma ester). N-BOC-O$^\alpha$-benzyl-glutamate (4.5 g, 13.3 mol) and 9-fluorenylmethanol (2.5 g, 12.5 mmol) were dissolved in 100 ml DCM. The solution was stirred and chilled in an ice bath. To the solution, 15.5 mg (0.13 mmol) of 4-(dimethylamino)pyridine and 2.75 g (13.3 mmol) of DCC were added, and the resulting mixture was stirred for 4 hr with continued cooling. Precipitated N,N'-dicyclohexylurea was filtered off and filtrate was diluted with 200 ml DCM. The solution was extracted and treated in the same manner as was for the aspartate described above. This yielded N-BOC-O$^\alpha$-benzyl-O-fluorenylmethylglutamate (gamma ester) (4.2 g), with a melting point of 97°–99.5° C.

4.0 g (7.75 mmol) of the foregoing product was hydrogenated over 125 mg of 10% Pd/C in 200 ml mixture of MeOH/EtOH/IPA (2:1:1) for 2 hr at room temperature at 40 psi. The reaction mixture was filtered to remove the catalyst, and concentrated to an oily residue. The residue was then mixed with 150 ml diethyl ether and extracted with 75 ml 5% citric acid and 75 ml H$_2$O. The combined aqueous layers were back-extracted with diethyl ether (2×40 ml). The combined ether layers were dried over MgSO$_4$, filtered, and concentrated to a white form. N-BOC-O-fluorenylmethyl-glutamate (gamma ester) (2.3 g) was obtained by recrystallizing the crude residue from diethyl ether/petroleum ether (1:10), melting point 123.5°–126° C.

(b) Synthesis of protected EGRGDSPKSS peptide sequence

Synthesis of the above peptide was performed using, in conjunction, an automated peptide synthesizer (System 990, Beckman Instruments, Inc., Palo Alto, Calif.) and a manual peptide synthesis apparatus (S.C. Glass Tech, Bonica, Calif.).

BOC-Ser(Bzl)OCH$_2$-PAM resin (1.0 g, 0.75 mmol) from Applied Biosystems (Foster City, Calif.) was used as the starting resin. The following amino acids were used in the synthesis: BOC-L-Ser(benzyl), BOC-L-Lys(N$^\epsilon$-FMOC), BOC-L-Pro, BOC-L-Asp(O-benzyl), BOC-Gly, BOC-Arg(N$^g$-tos), and BOC-Glu(Fm). Excess amino acid (2–3 fold) was used for each coupling. The peptide chain was constructed on the Beckman peptide synthesizer using BOC chemistry with the stepwise addition of each amino acid following the standardized cycle similar to that presented in Table 3, with adjustments for scale. 50% TFA in DCM, 5% DIEA in DCM, and 0.5 M of DCC in DCM were used as deprotecting agent, neutralizer, and activating agent, respectively, for each coupling.

(c) Capping of peptide sequence

Following the removal of the BOC group from the N-terminal Glu with 50% TFA in DCM, and neutralization with 5% DIEA in DCM, the protected peptide on resin was transferred to a manual apparatus for the terminal acetylation, or "capping". The N-terminal deprotected side chain protected peptide on resin was washed with MeOH (2×1 min), DCM (3×1 min); neutralized with 5% DIEA again in DCM (1×1 min, 1×20 min); washed with DCM (3×1 min); and acetylated (capped) with 50% Ac$_2$O in DCM (1 min wash, 20 min acetylation). The peptide then was cyclized by forming an amide linkage between the δ-carboxyl group of Glu and the ε-amino group of Lys by the general procedure below.

(d) General cyclization procedure for formation of the amide bridge

After the construction of the peptide chain, the amidating cyclization was carried out according to the following protocol. Filtering was performed between each step: (1) MeOH (2×1 min); (2) DCM (3×1 min); (3) 20% piperidine in DMF, wash for 1 min, and deprotection for 20 min; (4) DMF (2×1 min); (5) MeOH (2×1 min); (6) DCM (3×1 min); (7) BOP reagent (4 equiv.) in DMF (20 ml/gram of resin), stir for 2 min, and add DIEA (2% of DMF volume), stir for 4 hrs (the completion of the cyclization reaction was monitored by the ninhydrin test; if the reaction was judged incomplete at 4 hrs, the reaction was continued until the ninhydrin test was negative); (8) DMF (2×1 min); (9) DCM (2×1 min); (10) MeOH (2×1 min).

The final cyclic compound was removed from the resin by treatment with HF in the presence of 10% anisole for 1 hr at 0° C. After evaporation of the HF, the residue was washed with diethyl ether and extracted from the resin with 5% HOAc in H$_2$O. The aqueous extract was lyophilized to yield the crude peptide (730 mg).

(e) Purification

The compound was purified using a Waters Delta Prep 3000 system (Waters, Milford, Ma.) equipped with a C$_{18}$ column, using a linear gradient of increasing acetonitrile concentration in TEAP (pH 2.2 to 2.4) as the mobile phase. The collected fractions of the pure compound were pooled and applied again to the C$_{18}$ column. This time the sample was eluted with 0.5% HOAc to convert the phosphate salt form of the peptide to the desired acetate form. The pure peptide fractions were pooled, concentrated in vacuo, redissolved in water and lyophilized to give 92.9 mg of peptide, 98.7% HPLC purity, white powder.

EXAMPLE 5

Synthesis of Amide-Linked Cyclic Compounds (Backbone-Side Chain Linkage)

In this example, the following compound was synthesized:

The manual synthesis of the above compound began with 4-methylbenzhydrylamine resin (2.0 g, 1.4 mmol) from CBA, Inc. (Boulder, Col.). The peptide chain was assembled by using the BOC procedure described in the synthesis of the compound of Example 4 above. BOC-L-Asp(Fm), BOC-L-Pro, BOC-L-Ser(Benzyl), BOC-Gly, BOC-L-Arg($N^g$-tosyl) and N-FMOC-Gly were used in the synthesis.

The cyclization between the terminal amino group of Gly and the $\beta$-carboxyl group of $Asp^7$ was performed according to the general amide cyclization procedure described in the preceding Example 4.

The cyclic compound then was cleaved from the resin by HF and 10% anisole for 1 hr at 0° C. Following evaporation of the HF, the mixture was washed with diethyl ether (ether layer discarded) and extracted with 1N HOAc. The aqueous extract was lyophilized to yield 1.23 g of the crude compound.

Purification of the compound was achieved using a Waters preparative HPLC system with a $C_{18}$ column, following the method described in the preceding example. Yield was 678 mg pure product compound, HPLC purity of 99.7%, white powder.

EXAMPLE 6

Synthesis of Amide Linked Cyclic Compounds (Cyclization Prior to Complete Chain Assembly In this example, the following compound is synthesized:

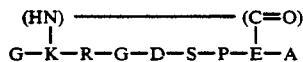

Here, cyclization can be performed when the chain is partially assembled, using orthogonal protection methods as described above. FIG. 1b is a diagram representing suitable procedures. The chain is partially assembled using the DCC method (Table 3) with primarily BOC protection until the BOC-Lys(FMOC), representing $L^1$ in the eventual product compound, is added. The BOC-Glu(Fm) and BOC-Lys(FMOC) are substituted for BOC-Glu(Chx) and BOC-Lys(Cl-Cbz). At this time the chain assembly is interrupted and the compound is cyclized while bound to the resin. Cyclization proceeds by treating the compound with 20% piperidine in DCM to deprotect the Glu and Lys residues, followed by filtering and washing, and by then by reaction with BOP in DMF and DIEA until the compound on the resin is ninhydrin negative. The amino-terminal glycine residue is then added to the cyclized compound, and the resulting product cleaved from the resin and worked up as described generally in the foregoing examples.

EXAMPLE 7

Synthesis of Cyclic Disulfide Compounds Containing RCD

In this example, the following compound was prepared:

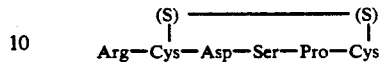

All amino acids, amino acid derivatives and amino acid mimetic were purchased from BACHEM (Torrance, Calif.). DCC was from Sigma Chemical Co. (St. Louis, Mo.). Trifluoroacetic acid was from Halocarbon Co. (New York, N.Y.). Triethyl-amine was from Fisher Scientific (Fair Lawn, N.J.). Other reagents were obtained from conventional sources and of analytical grade.

All peptides were synthesized by the solid phase method with a Beckman automated peptide synthesizer (System 990, Beckman Instruments, Inc., Palo Alto, Calif.) using BOC chemistry.

Attachment of N-BOC-S-p-methylbenzyl-L-cysteine (BOC-Cys(4-MeBzl)) to the chloromethylpolystyrene resin (Merrifield resin) was done in the presence of potassium fluoride. BOC-Cys(4-MeBzl) (0.9 molar eq.) was reacted with swelled Merrifield resin (Bio-Rad Lab., Richmond, Calif.) (1.0 molar eq.) in DMF in presence of KF (1.8 molar eq.) at 80° C. for 16 hr. The resin then was filtered, washed, and dried. The molar substitution of the resin was determined by weight.

The sequential elaboration of the peptide chain on the BOC-Cys(4-MeBzl) resin was carried out stepwise using the BOC procedure according the procedure in Table 5, below. At the end of the synthesis the N-terminal BOC protecting group was removed using TFA:DCM (1:1) for 30 min.

TABLE 5

Solid Phase Peptide Synthesis
For RCD-Containing Compounds
(TFA deprotection/DCC coupling)

| Step | Reagent | Vol* (ml) | Time** (min) |
|---|---|---|---|
| 1 | DCM wash (3x) | 20 | 1 |
| 2 | TFA-DCM (1:1) | 20 | 1 |
| 3 | TFA-DCM (1:1) | 20 | 20 |
| 4 | DCM wash (6x) | 20 | 1 |
| 5 | MeOH wash (2x) | 20 | 1 |
| 6 | DIEA-DCM (1:9) | 20 | 1 |
| 7 | DIEA-DCM (1:9) | 20 | 5 |
| 8 | MeOH wash (3x) | 20 | 1 |
| 9 | DCM wash (6x) | 20 | 1 |
| 10 | Boc-AA (3.2 mM, 2-fold excess) in DCM plus DCC in DCM (0.5 M) | | 120 |
| 11 | DCM wash (2x) | 20 | 1 |
| 12 | DCM-MeOH (1:1) (2x) | 20 | 1 |
| 13 | DIEA-DCM (1:9) | 20 | 1 |
| 14 | MeOH wash (2x) | 20 | 1 |
| 15 | DCM wash (2x) | 20 | 1 |
| 16 | $Ac_2O$ in DCM (1:3) | 20 | 20 |
| 17 | DCM wash (3x) | 20 | 1 |
| 18 | MeOH wash (2x) | 20 | 1 |

*The volume given is for the synthesis using 2 g of resin with the substitution of 0.8 mM/g of resin.
**All times given in repeated wash steps are "per wash".

Synthesis and Cleavage. For the synthesis of the title compound, the following amino acids were used: N-BOC-L-proline, N-BOC-L-serine(benzyl), N-BOC-L-aspartic acid-$\beta$-cyclohexyl ester, N-BOC-L-cysteine-(4- methylbenzyl), and N-BOC-N^g-tosyl-L-arginine. Starting with 2.0 g (1.6 mmol) N-BOC-Cys(4-MeBzl) resin and through the stepwise elaboration of the protected peptide chain, 3.4 g of the peptide resin was obtained. The peptide was removed from the resin by treatment with HF in presence of 10% anisole and 5% of dimethylsulfide for 1 hr. at 0° C. Following evaporation of the HF, the peptide resin residue was washed in turn with diethyl ether (discarded ether wash) and extracted with 5% HOAc in $H_2O$ (50 ml×4). The aqueous acetic acid solution was lyophilized to yield 780 mg of the crude, noncyclic peptide (Ellman test positive, Stewart and Young, *Solid Phase Peptide Synthesis*, 2nd ed. p. 116).

Cyclization. The formation of the intramolecular disulfide bridge was accomplished by using the iodine oxidation method. The crude peptide was dissolved in 300 ml of 80% acetic acid in $H_2O$. The peptide solution was titrated with $I_2$-glacial acetic acid (saturated) until the solution turned light brown in color, and stirred for 1-2 hr. at room temperature. The excess iodine was removed by adding ascorbic acid-water solution. The peptide solution was then concentrated in vacuo. The residue was redissolved in water and lyophilized to obtain the crude cyclic compound.

Purification. The compound was purified on a 25×2.5 cm SP Sephadex C-25 (Pharmacia LKB Biotechnology Inc., Piscataway, N.J.) column. The column was first equilibrated with 10 mM $NH_4OAc$ buffer (pH 3.5). The compound was eluted with $NH_4OAc$ buffer in a linear gradient of increasing $NH_4OAc$ concentration from 10–300 mM (pH 3.5–6.5). The fractions which contained the pure produce were pooled and lyophilized. The dried residue was redissolved in $H_2O$ and lyophilized thrice to ensure the removal of the $NH_4OAc$ salt to yield 106 mg produce (HPLC, 95% pure).

Other RCD Peptides. In a similar fashion, the following compounds of the invention are also synthesized:

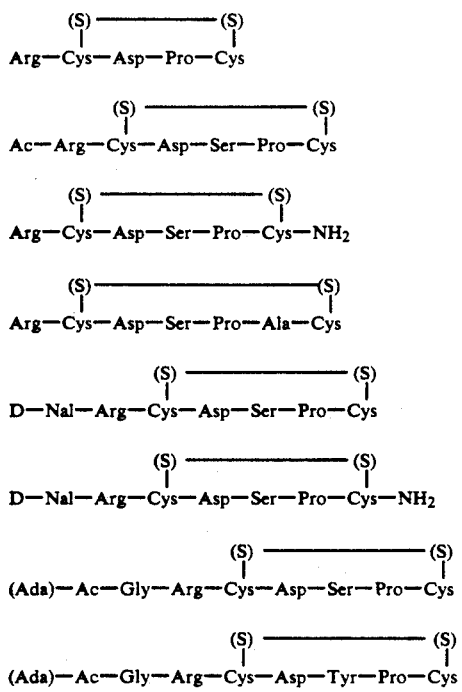

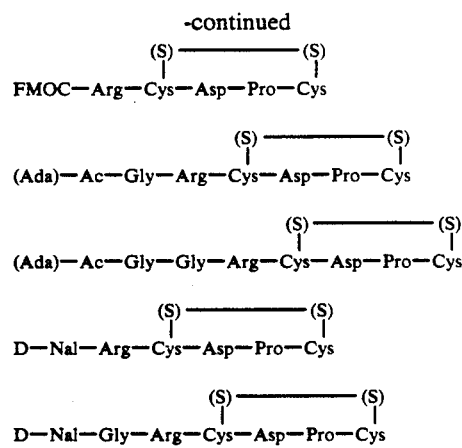

The peptides containing D-Nal are purified using a Waters Delta Prep 3000 system (Waters, Milford, Massachusetts) equipped with a $C_{18}$ column, using a linear gradient of increasing acetonitrile concentration in TEAP (pH 2.2 to 2.4) as the mobile phase. The collected fractions of the pure peptide are then eluted again with 0.5% HOAc in the same HPLC system to exchange the phosphate salt form of the peptide to the desired acetate form.

EXAMPLE 8

Synthesis of Peptide Bond Isostere Compounds

Cell adhesion modulation compounds containing peptide bond isostere structures of the following formulas were synthesized:

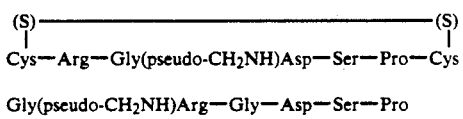

BOC amino acid aldehydes used in this synthesis were prepared by the method of J-A Fehrentz and B. Castro, Synthesis 676–678 (1983). The introduction of the pseudo $CH_2NH$ peptide bond was done by utilizing the reductive alkylation reaction in solid phase (Y. Sasaki and D.H. Coy, Peptides, 8:119–121 (1987)).

Preparation of BOC-Glycinal. Synthesis of BOC-glycinal from BOC-glycine involved the steps of forming the N-methoxy-N-methylamide of BOC-protected glycine, followed by reduction to the aldehyde compound. Since the aldehyde was highly reactive it was prepared immediately before use.

8.75 g (50 mmol) of BOC-glycine dissolved in 150 ml DCM and 6.95 ml (50 mmol) of TEA was added to the solution, and stirred. 17.42 g (50 mmol) BOP reagent (Richelieu Biotechnologies, QC, Canada) was added, followed a few minutes later with O,N-dimethylhydroxylamine hydrochloride (5.6 g, 55 mmol) and TEA (7.67 g, 55 mmol). The reaction was complete in 60 min, and the result was verified by TLC monitoring. A small amount of TEA was used to neutralize the mixture (adjust the pH to above 7.0) in order to allow the reaction go to completion. The mixture was diluted to 500 ml with DCM. The solution was washed in turn with 3N HCl (3×100 ml), saturated $NaHCO_3$ (3×100 ml), and brine (3×100 ml). The DCM layer was dried over $MgSO_4$ and concentrated to obtain the crude product. Recrystallization from water afforded 5.85 g $N^\alpha$-

(BOC)-glycine N-methoxy-N-methylamide (m.p. 92°-95° C.). This product was dried thoroughly in vacuo over $P_2O_5$ before use in the following reaction.

To obtain the BOC-glycinal (BOC-NH-$CH_2$-CHO), $LiAlH_4$ (569.3 mg, 15 mmol) was added to a stirred solution of the above compound (2.18 g, 10 mmol) in 100 ml anhydrous THF (Aldrich). Reduction was completed in 15 min. The mixture was hydrolyzed with a solution of $KHSO_4$ (2.72 g, 20 mmol) in $H_2O$ (50 mL). Then, the THF was evaporated, and the aqueous solution was extracted with diethyl ether (1×300 ml, 2×100 ml). The combined diethyl ether layers were washed in turn with 3N HCl (3×70 ml), 5% $NaHCO_3$ (3×50 ml), brine (1×70 ml), and dried over $MgSO_4$. The solution was concentrated to leave a light yellow oily residue, which was tested by IR for the presence of the desired aldehyde. The final product was redissolved in anhydrous diethyl ether and stored under $N_2$ gas at −20° C. until used.

Peptide Synthesis. All residues were incorporated by the solid phase method using the BOC procedure described earlier, except for the reduced bond isostere linkage which was prepared as described below. Following the introduction of the reduced bond isostere to the peptide on-resin, the remainder of the synthesis was continued as before. The peptide fragment preceding the $CH_2NH$ bond were assembled in a Beckman Peptide Synthesizer (System 990).

Introduction of the $CH_2NH$ bond. The following procedure was next carried out:

(1) The peptide-resin was transferred to a manual apparatus after the removal of the BOC group from the partially assembled peptide chain.

(2) The resin was washed in turn with DCM (3×1 min), MeOH (2×1 min), DCM (3×1 min), and DMF (2×1 min).

(3) BOC-glycinal (>3 equiv.) was added in 15 ml DMF containing 1% AcOH.

(4) 10 ml (10 mmol, 4 equiv.) of 1M $NaBH_3CN$ in THF (Aldrich) was added portion-wise in 30 min and further stirred for 1 hr for the reductive alkylation.

(5) The resin was washed in turn with DMF (2×1 min), DCM (3×1 min), MeOH (2×1 min), and tested for $NH_2$ content with the ninhydrin assay.

The coupling of the additional amino acids after the $CH_2NH$ bond was continued using the standard BOC procedure in a manual apparatus. The peptide was removed from the resin by treatment with HF in presence of 10% anisole and 5% dimethylsulfide for 1 hr at 0° C. The residue was washed with diethyl ether, filtered, and extracted with 1M HOAc in $H_2O$ (50 ml×4). The solution was lyophilized to yield the crude noncyclic peptide (780 mg).

Cyclization. With respect to the first title compound, the formation of the intramolecular disulfide bridge was accomplished by using iodine oxidation method. The noncyclic peptide (Ellman positive) was dissolved in 300 ml of 80% HOAc. The peptide solution was titrated with $I_2$-glacial acetic acid until the solution turned light brown in color, and stirred for 1-2 hr at room temperature. The excess iodine was removed by adding ascorbic acid-water solution. The peptide solution was then concentrated in vacuo. The residue was redissolved in water and lyophilized to obtain the crude cyclic peptide.

Both peptides were purified using techniques as described in the foregoing examples.

By using the synthetic techniques described above, cyclic compounds of the invention in which linkage (through $L^1$, $L^2$ and Z) includes a secondary amine structure may analogously be prepared. It is most advantageous, from a synthetic standpoint, to incorporate the isostere bond linkage prior to final cyclization of the compound. In such a case, cyclization is completed as a final step (after assembly of the desired residues including the isostere bond) through formation of, typically, a peptide bond at a point within the sequence 1-2-3-4-5-6.

2. Therapeutic Utility

In the practice of the therapeutic methods of the present invention, an effective amount of the active compound, including derivatives or salts thereof, or a pharmaceutical composition containing the same, as described below, is administered via any of the usual and acceptable methods known in the art, either singly or in combination with another compound or compounds of the present invention or other pharmaceutical agents such as immunosuppressants, antihistamines, corticosteroids, and the like. These compounds or compositions can thus be administered orally, sublingually, topically (e.g., on the skin or in the eyes), parenterally (e.g., intramuscularly, intravenously, subcutaneously or intradermally), or by inhalation, and in the form of either solid, liquid or gaseous dosage including tablets, suspensions, and aerosols, as is discussed in more detail below. The administration can be conducted in single unit dosage form with continuous therapy or in single dose therapy ad libitum.

Useful pharmaceutical carriers for the preparation of the pharmaceutical compositions hereof can be solids, liquids or gases; thus, the compositions can take the form of tablets, pills, capsules, powders, enterically coated or other protected formulations (such as by binding on ion exchange resins or other carriers, or packaging in lipid protein vesicles or adding additional terminal amino acids), sustained release formulations, solutions (e.g., ophthalmic drops), suspensions, elixirs, aerosols, and the like. Water, saline, aqueous dextrose, and glycols are preferred liquid carriers, particularly (when isotonic) for injectable solutions. The carrier can be selected from various oils including those of petroleum, animal, vegetable or synthetic origin, for example, peanut oil, soybean oil, mineral oil, sesame oil, and the like. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. The compositions may be subjected to conventional pharmaceutical expedients such as sterilization and may contain conventional pharmaceutical additives such as preservatives, stabilizing agents, wetting or emulsifying agents, salts for adjusting osmotic pressure, buffers, and the like. Suitable pharmaceutical carriers and their formulations are described in Martin, Remington's Pharmaceutical Sciences, 15th Ed. (Mack Publishing Co., Easton 1975) (see, e.g., pp. 1405-1412, 1461-1487). Such compositions will, in general, contain an effective amount of the active compound together with a suitable amount of carrier so as to prepare the proper dosage form for proper administration to the host.

In one preferred embodiment, the therapeutic methods of the present invention are practiced when the relief of symptoms is specifically required or perhaps imminent; in another preferred embodiment, the method hereof is effectively practiced as continuous or prophylactic treatment.

In the practice of the therapeutic methods of the invention, the particular dosage of pharmaceutical composition to be administered to the subject will depend on a variety of considerations including the nature of the disease, the severity thereof, the schedule of administration, the age and physical characteristics of the subject, and so forth. Proper dosages may be established using clinical approaches familiar to the medicinal arts. It is presently believed that dosages in the range of 0.1 to 100 mg of compound per kilogram of subject body weight will be useful, and a range of 1 to 100 mg per kg generally preferred, where administration is by injection or ingestion. Topical dosages may utilize formulations containing generally as low as 0.1 mg of compound per ml of liquid carrier or excipient, with multiple daily applications being appropriate.

The compounds and therapeutic or pharmaceutical compositions of the invention are useful in the study or treatment of diseases or other conditions which are mediated by the binding of integrin receptors to ligands, including conditions involving inappropriate (e.g., excessive or insufficient) binding of cells to natural or other ligands. Such diseases and conditions include inflammatory diseases such as rheumatoid arthritis, asthma, allergy conditions, adult respiratory distress syndrome, inflammatory bowel diseases (e.g., ulcerative colitis and regional enteritis) and opthalmic inflammatory diseases; autoimmune diseases; thrombosis or inappropriate platelet aggregation conditions, and cardiovascular disease; neoplastic disease including metastasis conditions; as well as conditions wherein increased cell binding is desired, as in wound healing or prosthetic implantation situations as discussed in more detail above.

In addition, derivatives of the present compounds may be useful in the generation of antigens which, in turn, may be useful to generate antibodies. These antibodies will, in some cases, themselves be effective in inhibiting cell adhesion or modulating immune activity by acting as receptors for matrix proteins or other cell adhesion ligands, or, if anti-idiotypic, by acting to block cellular receptors.

EXAMPLE 9

Cell Adhesion Inhibition Assay

The following assay established the activity of the present compounds in inhibiting cell adhesion in a representative in vitro system. The assay was a competition assay in which both fibronectin and a test compound were present. Microtiter plates were first precoated with fibronectin. The test peptide was then added in increasing concentrations with cells known to contain the fibronectin receptor. The plates were then washed and stained for quantitation of attached cells. The present assay directly demonstrates the anti-cell adhesion activity and modulatory activity of the present compounds. For example, by immobilizing the peptide on a surface, one could adhere appropriate cells to that surface. Other cell adhesion modulation activity, and utilities pertinent thereto, will be apparent to those skilled in the art.

The cell line U937 was purchased from American Type Tissue Culture Collection. The cells were cultured in RPMI media (J. R. Scientific Company, Woodland Hills, Calif. 95695) containing 10% fetal calf serum. Fibronectin was purified from human plasma according to the procedure of Engvall, E. and Ruoslahti, E., Int. J. Cancer 20: 1–4 (1977).

Microtiter plates (96-well, Falcon) were coated overnight at 4° C. with 5 µg/ml fibronectin (FN) (for a total volume of 0.1 ml) or, as a control, 5 µg/ml bovine serum albumin (BSA) diluted in phosphate buffered saline (PBS, 0.01 M $NaPO_4$ in 0.9% NaCl at pH 7.2 to 7.4). Unbound proteins were removed from plates by washing with PBS. The plates were then coated with 100 µl of PBS containing 2.5 mg/ml BSA for one hour at 37° C. This procedure is a modification of a previously published method, Cardarelli, P.M. and M.D. Pierschbacher, PNAS-USA 83: 2647-2651 (1986). The containment in the wells of functional amounts of immobilized protein has been confirmed by independent assay of fibroblast attachment and ELISA (Engvall, E., Methods Enzymol. 70: 419–439 (1980)), although the actual amount of protein bound to the plate in these assays was not determined.

A U937 culture was collected and washed two times with Hanks Balanced Salt Solution. The cells were counted and adjusted to $1.5 \times 10^6$ cells per ml in Dulbecco's Modified Eagles Medium (DMEM) plus BSA (2.5 mg/ml) for cell attachment assay. Subject compounds were then dissolved in DMEM and BSA, and the pH was adjusted to 7.4 with 7.5% sodium bicarbonate. The compounds (100 µl) were added to FN-coated wells, at 1.5, 0.75, 0.375, 0.188, 0.094, 0.047, 0.023, 0.012, 0.006 and 0.003 mg/ml final concentration and U937 cells (100 µl) were added per well. The plates were then incubated at 37° C. for 60 minutes. Following this incubation, the plates were washed once with PBS. Attached cells were fixed with 3% paraformaldehyde in PBS and stained with 0.5% toluidine blue in 3.7% formaldehyde. The cells were stained overnight at room temperature and the optical density at 590 nm of toluidine blue-stained cells was determined using a vertical pathway spectrophotometer to quantitate attachment (VMAX Kinetic Microplate Reader, Molecular Devices, Menlo Park, Calif. 94025).

Results. Table 6, below, shows the results of the cell adhesion inhibition assay. Potency is expressed in µM units. FIG. 2 is a diagram representing the curve of cell adhesion inhibition for the compound

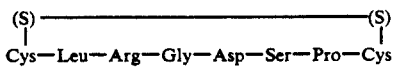

Cys—Leu—Arg—Gly—Asp—Ser—Pro—Cys

TABLE 6

ACTIVITY OF COMPOUNDS IN THE U937 - FIBRONECTIN ADHESION ASSAY[1]

| Peptide # | Sequence | $IC_{50}$, µM |
|---|---|---|
| 1 | C*LRGDSPC* | 909 |
| 2 | GC*LRGDSPC*—NH₂ | 468 |
| 3 | GC*L(homoArg)GDSPC*—NH₂ | 1000–1500 |
| 4 | C*GRGDSPC* | 597 |
| 5 | C*LRGDSP(Pen)*—NH₂ | 1000–1500 |
| 6 | C*(Nle)RGDSPC*—NH₂ | 383 |
| 7 | C*(dL)RGDSPC*—NH₂ | 924 |
| 8 | C*RGDC* | 1461 |
| 9 | C*RGDSC* | 1104 |
| 10 | C*RGDSPC* | 140 |
| 11 | (Mpr*)GRGDSPC* | 330 |
| 12 | (Mpr*)LRGDSPC* | 611 |
| 13 | (Mpr*)LRGDTPC* | 870 |

TABLE 6-continued
ACTIVITY OF COMPOUNDS IN THE U937 - FIBRONECTIN ADHESION ASSAY[1]

| Peptide # | Sequence | IC$_{50}$, μM |
|---|---|---|
| 14 | C*YRGDSPC* | 198 |
| 15 | C*GRGDVPC* | 494 |
| 16 | C*GRGDAPC* | 829 |
| 17 | EGRGDSPKSS | 1059 |
| 18 | Ac-E*GRGDSPK*SS | 171 |
| 19 | K*RGDSPD*SS | 1084 |
| 20 | (dC*)(dR)G(dD)(dS)(dP)(dC*) | 597 |
| 21 | C*(Sar)RGDSPC* | 136 |
| 22 | G*RGDSPD*—NH$_2$ | 112 |
| 23 | (Ada)-Ac-C*GRGDSPC* | 272 |
| 24 | VTC*GRGDSPC*A—NH$_2$ | 50 |
| 25 | VSC*GRGDSPC*A—NH$_2$ | 636 |
| 26 | (dC*)(dP)(dS)(dD)G(dR)(dC*) | 1161 |
| 27 | C*RGDSPC*—NH$_2$ | 242 |
| 28 | A(norVal)SC*GRGDSPC*A—NH$_2$ | 632 |
| 29 | C*GRGD[Thr(OCH$_3$)]PC* | 255 |
| 30 | C*YRGDSPC*—NH$_2$ | 1024 |
| 31 | C*GRGDSPC*—NH$_2$ | 2719 |
| 32 | (Mpr*)YRGDSPC* | 240 |
| 33 | (Mpr*)RGDSPC* | 231 |
| 34 | (d-Nal)-C*RGDSPC* | 236 |
| 35 | RC*DSPC* | 1040 |
| 36 | C*RGDYPC* | 30 |
| 37 | (Ada)-Ac-GGGC*RGDSPC* | 85 |
| 38 | (Ada)-Ac-GGC*RGDSPC* | 45 |
| 39 | (Ada)-Ac-GC*RGDSPC* | 58 |
| 40 | d-Nal-C*RGDSPC* | 136 |
| 41 | (PMP)*-RGDSPC* | 227 |
| 42 | (FMOC)-RC*DPC* | 107 |
| 43 | Sar*RGDSPD* | 103 |
| 44 | C*RGDTPC* | 91 |
| 45 | C*YRGDVPC*-Aib—NH$_2$ | 106 |
| 46 | R*GDSPE*—NH$_2$ | 91 |
| 47 | G*RGDSPD*—NH$_2$ | 134 |
| 48 | R*GDSPD* | 60 |
| 49 | RC*DPC* | 32 |
| 50 | C*RGDFPC* | 35 |
| 51 | (Ada)-Ac-GGC*RGDY-3-thioPro-C*—NH$_2$ | 6.8 |
| 52 | (Ada)-Ac-GGC*RGDYPC*—NH$_2$ | 15 |
| 53 | (Ada)-CA-GGC*RGDY-3-thioPro-C*—NH$_2$ | 25 |
| 54 | (Ada)-CA-GGC*RGDYPC*-NH$_2$ | 39 |
| 55 | (Ada)-Ac-GGC*RGDVPC* | 30 |
| 56 | (Ada)-Ac-GC*RGDVPC* | 54 |
| 57 | (Ada)-Ac-C*RGDVPC* | 115 |
| 58 | (Ada)-Ac-GGC*RGDYPC* | 42 |
| 59 | (Ada)-Ac-GC*RGDYPC* | 81 |
| 60 | (FMOC)-GGC*RGDSPC* | 53 |
| 61 | (Ada)-Ac-GC*RGDSPC*—NH$_2$ | 86 |
| 62 | C*RGDS(1,1-ACC)C* | 148 |

[1]Asterisk ("*") following residue abbreviation designates linking residue that provides functional group for cyclization. Functional group precursors are as follows: C*, side chain sulfhydryl; Pen*, side chain sulfhydryl; Mpr, 3-mercapto (sulfhydryl) group; K*, side chain amino grup; D*, side chain carboxyl group; G*, α-amino group; R*, side chain (guanidino) amino group. "d" indicates the D-enantiomer.

In addition, the compound

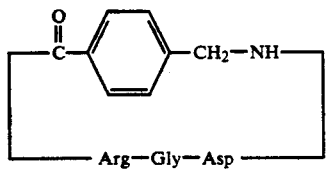

was tested and found to have an IC$_{50}$ of 251 μM.

The following compounds of Table 7 have also been synthesized and tested in the cell adhesion inhibition assay described above. Specific activity levels were not established inasmuch as the IC$_{50}$ of the compounds was determined to be in excess of 1.5 mg/ml. Thus, although such compounds are believed to be active as cell adhesion modulators at higher dosage levels, they are presently not as highly preferred as the compounds exemplified above.

TABLE 7
ADDITIONAL COMPOUNDS[2]

| Sequence |
|---|
| (Pen*)LRGDSPC* |
| AcGC*LRGDSPC*—NH$_2$ |
| C*LRGESPC* |
| (Pen*)LRGDSP(Pen*)—NH$_2$ |
| C*GRGDC* |
| C*GRGDSC* |
| C*VRGDSPC |
| C*(norVal)RGDSPC* |
| C*IRGDSPC* |
| YC*LRGDSPC*—NH$_2$ |
| LC*LRGDSPC*—NH$_2$ |
| FC*LRGDSPC*—NH$_2$ |
| LC*LRGDSPC* |
| FC*LRGDSPC* |
| YC*LRGDSPC* |
| (D-Nal)C*LRGDSPC* |
| C*GRGD(Sar)PC* |
| C*GRGDS(Hyp)C* |
| C*GRGDS(homoPro)C* |
| C*GRGDS(Dhp)C* |
| C*(dR)G(dD)(dS)(dP)C* |
| C*TRYRGDQDATMSC* |
| C*(Nic-Lys)GDSPC* |
| C*FRGDSPC* |
| R*GDSPD*—NH$_2$ |
| Ac-D*RGDSPK*—NH$_2$ |

[2]See notes to Table 6.

Thus, an aspect of the present invention is to provide compounds having extraordinarily high potencies in modulating cell adhesion to integrin receptors, including specifically inhibition of cell adhesion to the fibronectin receptor. In one regard, the present invention includes compounds having an IC$_{50}$ of less than about 500 μM as established in a U937 fibronectin adhesion assay; and in another regard, the invention includes compounds having an IC$_{50}$ of less than about 100 μM in such assay. The invention also includes methods for obtaining (either in vitro or in vivo) such fibronectin receptor adhesion inhibition, and integrin receptor adhesion inhibition generally, using disclosed compounds, at desirably low concentrations, having an IC$_{50}$ of less than about 500 μM, or alternately less than about 100 μM. Likewise, another aspect of the invention is to provide such compounds, and such methods for obtaining integrin receptors adhesion inhibition, with IC$_{50}$ potency levels at least as low as about 1 μM, and alternately at least as low as about 6.8 μM.

The foregoing examples are given to enable those skilled in the art to more fully understand and practice the present invention. They should not be construed as a limitation upon the scope of the invention, which is set forth in the appended claims but merely as being illustrative and representative thereof.

What is claimed is:

1. A compound of the formula

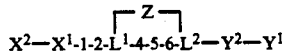

and pharmaceutically acceptable salts thereof, wherein
L$^1$ and L$^2$ are each, or are together, a residue of an amino acid, an amino acid analog or an amino acid mimetic having a functional group suitable for the formation of a cyclizing bridge between L$^1$ and L$^2$;
Z is a cyclizing moiety or bond between L$^1$ and L$^2$;

1 is optional and, where present, is selected from the group consisting of Leu, Sar, D-Nal, Tyr, Phe, Ile, Pro, Gly, Ala, Val, norLeu, norVal, β-Ala, Trp, and (Ada -Ala;

2 is selected from the group consisting of Arg, homoArg and norArg.

4 is selected from Asp and, where 2 is norArg, Glu.

5 is optional and, where present, is selected from the group consisting of Ser, Thr, Tyr, Trp, Ala, Val, Phe $$-Tyr-,\ -Thr-,\ -Ser-\ \text{and}\ -NH-CH-\overset{(CH_2)_m-OR'}{\underset{\underset{O}{\|}}{|}}C-$$
$$\phantom{-Tyr}|\phantom{,\ -Thr}|\phantom{,\ -Ser}|$$
$$(OR')\ (OR')\ (OR')$$

wherein m is 2, 3 or 4;

6 is optional and, where present, is selected from the group consisting Pro, 3-thioPro, 1,1-ACC, Dhp, Hyp, homoPro and Phe;

$X^1$ and $Y^1$ are each optional and, where present, are independently selected from sequences of 1 to 4 D- or L-amino acids or amino acid analogs;

$X^2$ is an optional $N^\alpha$-substituent selected from R'-(including hydrogen) and R'CO—; and $Y^2$ is an optional carboxyl terminal substituent selected from the group consisting of —OR' (including hydroxy), —NR'$_2$ (including —NH$_2$ and —NHR'), —NHNH$_2$ and —SR';

and wherein each R' is individually a pharmaceutically suitable substituent group, preferably one selected from the group consisting of hydrogen, linear and branched, unsubstituted and substituted $C_1$-$C_8$ lower alkyls, $C_2$-$C_8$ alkenyls, $C_2$-$C_8$ alkenyls, $C_2$-$C_8$ alkynyls, $C_6$-$C_{14}$ aryls, $C_7$-$C_{14}$ alkaryls, $C_7$-$C_{14}$ alkaryls and $C_3$-$C_{14}$ cycloalkyls, and, in the case of —NR'$_2$, from cyclized groups forming (in an attachment with the nitrogen atom) a 5-8 membered heterocyclic ring optionally containing oxygen, nitrogen or sulfur as a further ring heteroatom.

2. A compound of claim 1 wherein $L^1$ and $L^2$ each provide a sulfur-containing functional group, and cyclization is achieved through a disulfide bond.

3. A compound of claim 1 wherein $L^1$ is Cys.

4. A compound of claim 1 wherein $L^1$ and $L^2$ each provide sulfur-containing functional groups, and Z is a hydrocarbon bridge between said sulfur groups.

5. A compound of claim 1 wherein the linkage between $L^1$ and $L^2$ is a monosulfide linkage.

6. A compound of claim 1 wherein Z is a diketo, a diamino or a keto-amino moiety.

7. A compound of claim 6 wherein Z is a diketo moiety of the form $$-\overset{O}{\underset{\|}{C}}-(CH_2)_n-\overset{O}{\underset{\|}{C}}-$$

wherein n, is from 1 to 8.

8. A compound of claim 1 wherein Z is a diamino moiety of the form $$-NH-(CH_2)_n-NH-$$

n is an integer of from 1 to 8.

9. A compound of claim 1 wherein $L^1$ is directly bonded to $L^2$ via an amide bond.

10. A compound of claim 1 wherein the sequence 1-2-$L^1$-4-5-6-$L^2$ is selected from the group consisting of
Leu-Arg-Cys-Asp-Ser-Pro-Cys,
Arg-Cys-Asp-Ser-Pro-Cys, and
Arg-Cys-Asp-Pro-Cys.

11. A compound of claim 1 selected from the group consisting of $$\overset{(S)\phantom{xxxxxxxxxxxx}(S)}{\underset{Leu-Arg-Cys-Asp-Ser-Pro-Cys}{|\phantom{xxxxxxxxxxxxxxxx}|}}$$

$$\overset{(S)\phantom{xxxxxxxxx}(S)}{\underset{Arg-Cys-Asp-Ser-Pro-Cys}{|\phantom{xxxxxxxxxxxx}|}}$$

$$\overset{(S)\phantom{xxxxx}(S)}{\underset{Arg-Cys-Asp-Pro-Cys\ and}{|\phantom{xxxxxxxx}|}}$$

$$\overset{(S)\phantom{xxxxxxx}(S)}{\underset{FMOC-Arg-Cys-Asp-Pro-Cys}{|\phantom{xxxxxxxxxxxxxx}|}}$$

12. A compound of claim 1 useful in modulating adhesion of a cell expressing a fibronectin receptor.

13. A pharmaceutical composition comprising a compound of claim 1.

14. A compound of claim 1 having an $IC_{50}$ in a U937 fibronectin adhesion assay of less than about 500 μM.

15. A compound of claim 1 having an $IC_{50}$ in a U937 fibronectin adhesion assay of less than about 100 μM.

* * * * *